(12) United States Patent
Yoshioka

(10) Patent No.: US 12,207,944 B2
(45) Date of Patent: Jan. 28, 2025

(54) LAMINATE FOR BIOSENSOR AND BIOSENSOR

(71) Applicant: NITTO DENKO CORPORATION, Ibaraki (JP)

(72) Inventor: Ryoma Yoshioka, Ibaraki (JP)

(73) Assignee: NITTO DENKO CORPORATION, Ibaraki (JP)

( * ) Notice: Subject to any disclaimer, the term of this patent is extended or adjusted under 35 U.S.C. 154(b) by 1097 days.

(21) Appl. No.: 16/980,750

(22) PCT Filed: Mar. 11, 2019

(86) PCT No.: PCT/JP2019/009616
§ 371 (c)(1),
(2) Date: Sep. 14, 2020

(87) PCT Pub. No.: WO2019/176839
PCT Pub. Date: Sep. 19, 2019

(65) Prior Publication Data
US 2021/0000420 A1    Jan. 7, 2021

(30) Foreign Application Priority Data

Mar. 16, 2018 (JP) .................. 2018-049009
Mar. 8, 2019 (JP) .................. 2019-042390

(51) Int. Cl.
*A61B 5/00* (2006.01)

(52) U.S. Cl.
CPC .......... *A61B 5/6832* (2013.01); *A61B 5/6801* (2013.01); *A61B 5/683* (2013.01); *A61B 5/6833* (2013.01); *A61B 2562/18* (2013.01)

(58) Field of Classification Search
CPC ..... A61B 5/6832; A61B 2562/18; A61B 5/68; A61B 5/6801; A61B 5/683; A61B 5/6833;
(Continued)

(56) References Cited

U.S. PATENT DOCUMENTS 5,813,981 A * 9/1998 Carim .................. A61B 5/25
600/372
2003/0224160 A1   12/2003 Murakami et al.
(Continued)

FOREIGN PATENT DOCUMENTS

CN    101681216 A    3/2010
EP    3 003 139 A2   4/2016
(Continued)

OTHER PUBLICATIONS

Office Action issued on Aug. 2, 2022, for corresponding Japanese Patent Application No. 2019-042390, along with an English machine translation.
(Continued)

*Primary Examiner* — Linda C Dvorak
*Assistant Examiner* — Bradford C. Blaise
(74) *Attorney, Agent, or Firm* — Hauptman Ham, LLP

(57) ABSTRACT

A laminate for biosensor includes a pressure-sensitive adhesive layer for attaching to a surface of a living body; and a substrate layer disposed on the upper face of the pressure-sensitive adhesive layer, wherein the laminate for biosensor includes a probe disposed at the lower face of the laminate for biosensor, and a moisture barrier layer disposed so as to overlap with the probe when projected in the thickness direction.

7 Claims, 20 Drawing Sheets

(58) Field of Classification Search
CPC ..... A61B 5/68335; A61B 5/257; A61B 5/259; A61B 5/265; A61B 5/266; A61B 5/282
See application file for complete search history.

(56) References Cited

U.S. PATENT DOCUMENTS

| | | | |
|---|---|---|---|
| 2010/0159183 | A1 | 6/2010 | Nishimura |
| 2015/0305677 | A1 | 10/2015 | Berg et al. |
| 2016/0355712 | A1 | 12/2016 | Schuh et al. |
| 2017/0027516 | A1 | 2/2017 | Konno et al. |
| 2017/0288171 | A1* | 10/2017 | Ito .................... C23C 16/509 |
| 2017/0301698 | A1 | 10/2017 | Smith et al. |
| 2018/0049698 | A1* | 2/2018 | Berg .................... A41D 1/005 |
| 2018/0192948 | A1 | 7/2018 | Okumura et al. |
| 2018/0199443 | A1 | 7/2018 | Okumura et al. |
| 2019/0223749 | A1* | 7/2019 | Toth .................... A61B 5/6833 |

FOREIGN PATENT DOCUMENTS

| | | |
|---|---|---|
| JP | 2000-502581 A | 3/2000 |
| JP | 2003-342541 A | 12/2003 |
| JP | 2012-10978 A | 1/2012 |
| JP | 2014-87542 A | 5/2014 |
| JP | 2017-22236 A | 1/2017 |
| JP | 2017-22237 A | 1/2017 |
| JP | 2017-29241 A | 2/2017 |
| JP | 2017-66271 A | 4/2017 |
| TW | 201710436 A | 3/2017 |
| WO | 97/24061 A1 | 7/1997 |
| WO | 2007/092290 A2 | 8/2007 |
| WO | 2014/197822 A2 | 12/2014 |

OTHER PUBLICATIONS

Extended European Search Report issued on Nov. 5, 2021 for corresponding European Patent Application No. 19767263.7.
International Search Report issued for corresponding International Patent Application No. PCT/JP2019/009616 on Jun. 4, 2019, along with an English translation.
International Preliminary Report on Patentability issued for International Patent Application No. PCT/JP2019/009616 on Oct. 1, 2020, along with an English translation.
Office Acton issued on Aug. 11, 2022 for corresponding Taiwanese Patent Application No. 108108612, along with an English translation (10 pages).
Office Action issued on Aug. 30, 2023 for corresponding Chinese Patent Application No. 201980018041.4, along with an English translation (16 pages).

* cited by examiner

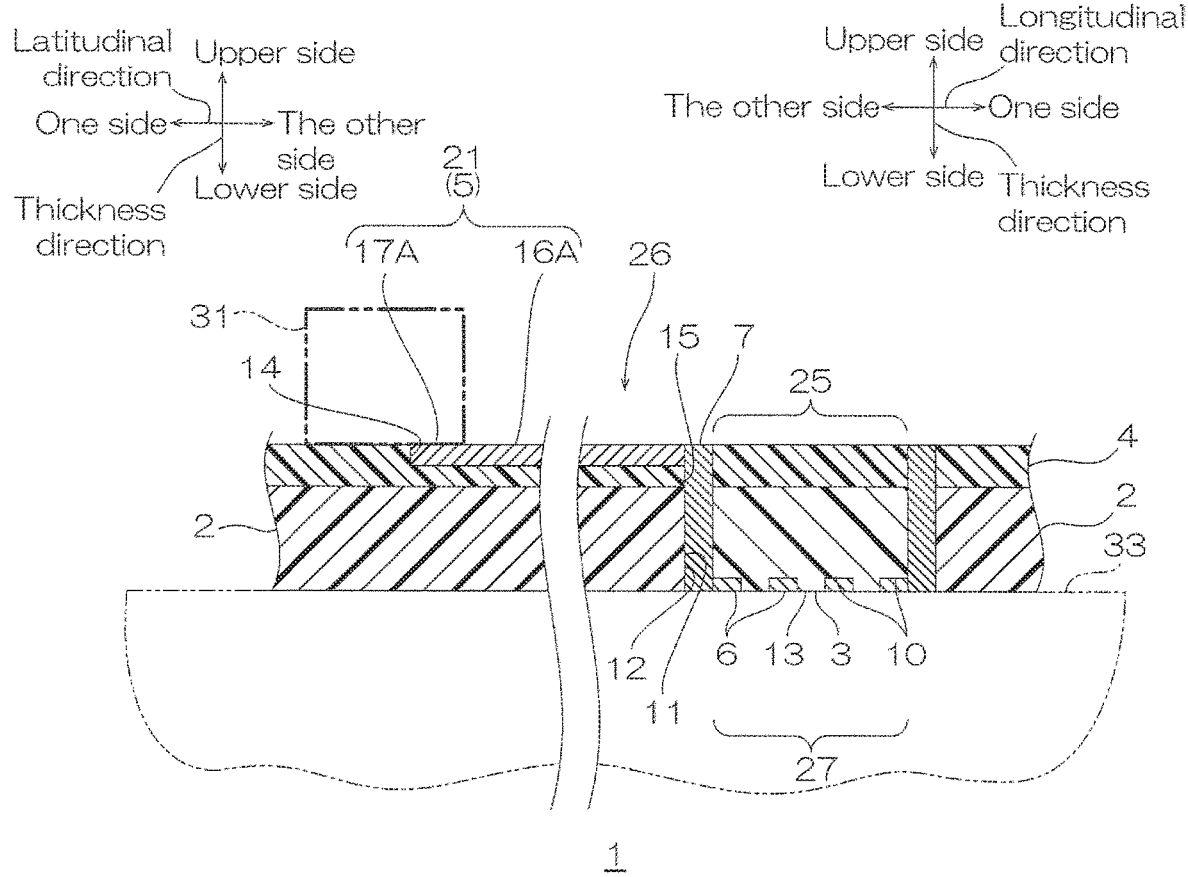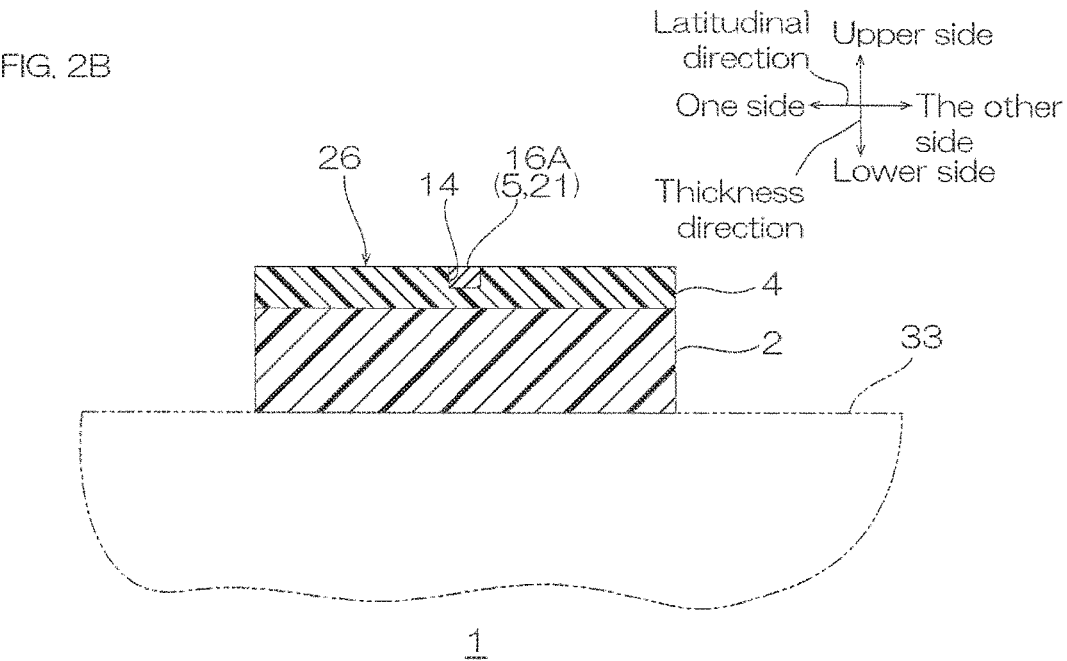

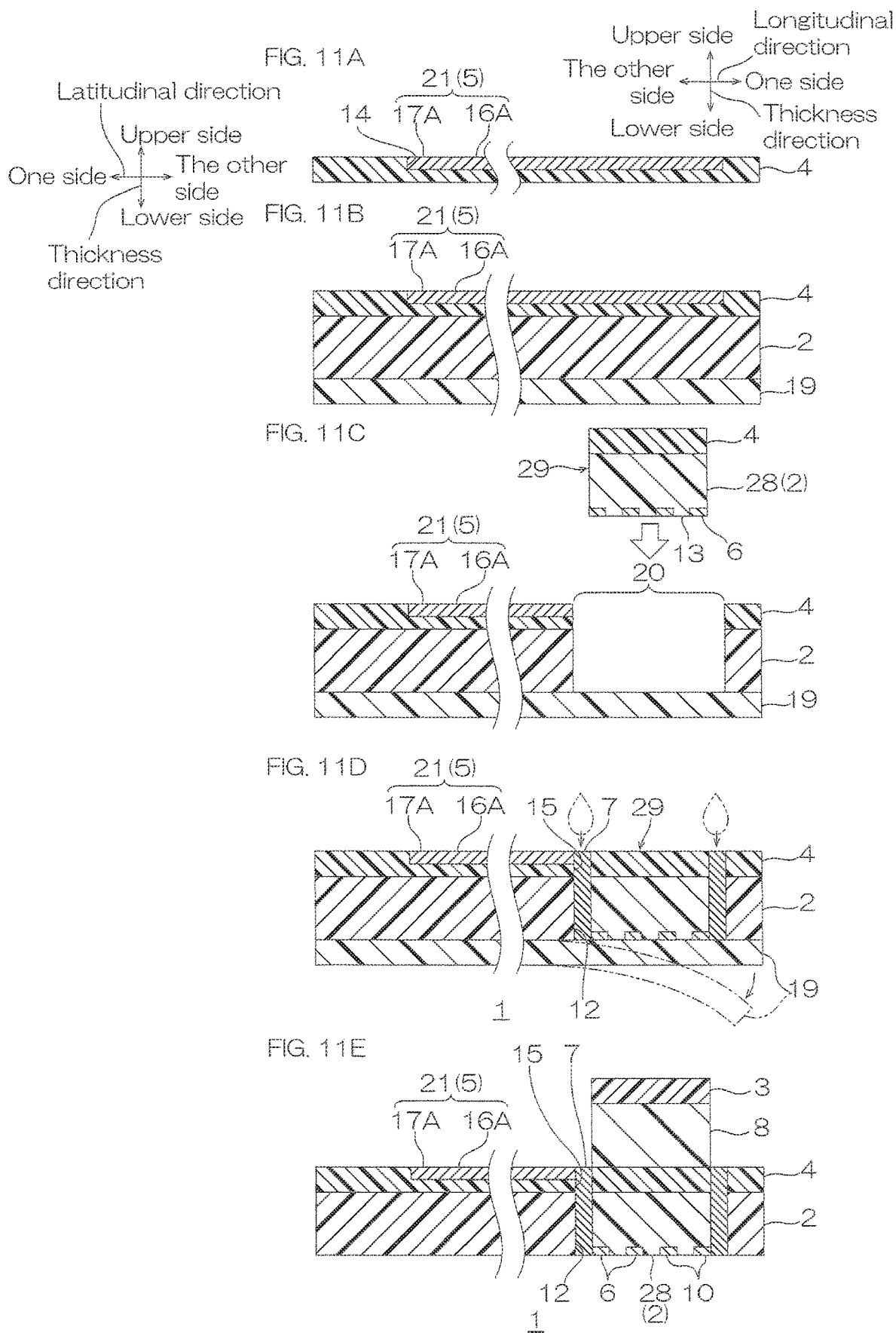

50b

LAMINATE FOR BIOSENSOR AND BIOSENSOR

CROSS REFERENCE TO RELATED APPLICATION

This application claims the priority of Japanese Patent Application Nos. 2018-049009, filed on Mar. 16, 2018 and 2019-042390 filed on Mar. 8, 2019, in the JPO (Japanese Patent Office). Further, this application is the National Phase Application of International Application No. PCT/JP2019/009616, filed on Mar. 11, 2019, which designates the United States and was published in Japan. Both of the priority documents are hereby incorporated by reference in their entireties.

TECHNICAL FIELD

The present invention relates to a laminate for biosensor and a biosensor; to be specific, a laminate for biosensor for various use including medical use and hygienic material use, and a biosensor.

BACKGROUND ART

Conventionally, a biosensor that is attached to the skin of a living body such as humans and detects biosignals has been known.

For such a biosensor, for example, Patent Document 1 has proposed a biocompatible polymer substrate including an adhesive first layer; a second layer disposed on an upper face thereof; an electrode that is disposed at a lower face of the second layer and makes contact with skin, a data input module disposed on the upper face of the first layer, and a wire disposed on the upper face of the second layer and connecting the electrode and module.

In such a biocompatible polymer substrate, the first layer is attached to the human skin, the electrode makes contact with the skin and detects the biosignals, such as voltage signals from the heart muscles via the skin, and the data input module receives and records the voltage signals from the heart muscles.

CITATION LIST

Patent Document

Patent Document 1: Japanese Unexamined Patent Publication No. 2012-10978

SUMMARY OF THE INVENTION

Problem to be Solved by the Invention

Meanwhile, when the surface of the electrode that is making contact with the skin of a living body gets dry, the electrode impedance rises to increase noises. Therefore, it has been examined to moisturize the interface between the electrode and skin with moisture to make lower electrode impedance.

However, when the biosensor is attached to the skin of a living body and used for a long period of time, the moisture steadily permeates into the biosensor and evaporates, and the electrode surface gets dry non-uniformly. As a result, an excessive increase and a large variation in the electrode impedance disadvantageously occur.

The present invention provides a laminate for biosensor and a biosensor that suppress increase and variation in electrode impedance.

Means for Solving the Problem

The present invention [1] includes a laminate for biosensor including a pressure-sensitive adhesive layer for attaching to a living body; and a substrate layer disposed on the upper face of the pressure-sensitive adhesive layer, wherein the laminate for biosensor includes a probe disposed at the lower face of the laminate for biosensor, and a moisture barrier layer disposed so as to overlap with the probe when projected in the thickness direction.

With this laminate for biosensor, the moisture barrier layer is disposed so as to overlap with the probe. Therefore, when the laminate for biosensor is attached to the skin of a living body, the moisture barrier layer can suppress moisture present at the interface between the living body and the probe to permeate the laminate for biosensor in the thickness direction. As a result, the moisture can be kept uniformly at the lower face of the probe, and dryness of the probe can be suppressed uniformly. Therefore, increase and variation in the electrode impedance can be suppressed.

The present invention [2] includes the laminate for biosensor of [1], wherein the moisture barrier layer has a moisture permeability of 600 $g/m^2 \cdot day$ or less.

With this laminate for biosensor, the moisture barrier layer has a low moisture permeability, and therefore increase in impedance and impedance variation can be suppressed even more reliably.

The present invention [3] includes the laminate for biosensor of [1] or [2], wherein the moisture barrier layer is disposed at a side upper than the lower face of the probe.

With this laminate for biosensor, the moisture barrier layer is disposed at a side upper than the lower face of the probe. Therefore, compared with the laminate for biosensor, in which the moisture barrier layer is disposed at the side lower than the lower face of the probe, the material of the moisture barrier layer can be selected more freely, and a material with high moisture barrier properties can be selected. Furthermore, the entire lower face of the laminate for biosensor can be made flat, and therefore it can be attached to a living body excellently.

The present invention [4] includes the laminate for biosensor of any one of [1] to [3], wherein the moisture barrier layer is disposed inside the pressure-sensitive adhesive layer.

With this laminate for biosensor, the moisture barrier layer is disposed inside the pressure-sensitive adhesive layer, and therefore the moisture barrier layer is disposed at a position near the probe. Therefore, the moisture can be kept uniformly and more reliably at the lower face of the probe.

The present invention [5] includes the laminate for biosensor of [4], wherein the moisture barrier layer has pressure-sensitive adhesiveness.

With this laminate for biosensor, the moisture barrier layer has pressure-sensitive adhesiveness, and therefore can adhere to the probe and the substrate layer pressure-sensitively; and detachment of the moisture barrier layer can be reliably suppressed. When the probe has an exposure region, the lower face of the moisture barrier layer can be exposed at the exposure region of the probe, and attached to a living body with pressure-sensitive adhesion. Therefore, the probe can be reliably brought into contact with a living body uniformly, and more reliable sensing can be achieved.

The present invention [6] includes the laminate for biosensor of any one of [1] to [5], wherein the moisture barrier layer is disposed at the upper side of the substrate layer.

With this laminate for biosensor, the moisture barrier layer is disposed at the upper side of the substrate layer, and therefore the moisture barrier layer can be easily disposed at the upper side of the substrate layer through the pressure-sensitive adhesive layer. Therefore, it is excellently suitable for production.

The present invention [7] includes the laminate for biosensor of any one of [1] to [6], wherein the moisture barrier layer is at least one resin layer selected from the group consisting of a rubber resin layer, polystyrene resin layer, polyolefin resin layer, acrylic resin layer, and poly vinyl alcohol resin layer.

With this laminate for biosensor, the moisture barrier layer is a specific resin layer, and therefore increase in impedance and impedance variation can be more reliably suppressed.

The present invention [8] includes the laminate for biosensor of any one of [1] to [7], wherein the probe has an exposure region that allows the pressure-sensitive adhesive layer or the moisture barrier layer to be exposed.

With this laminate for biosensor, the probe has an exposure region, so that the pressure-sensitive adhesive layer or the moisture barrier layer having pressure-sensitive adhesiveness is allowed to be exposed at the exposure region in the lower face side of the laminate for biosensor.

Therefore, the entire probe can be brought into contact with a living body. As a result, more reliable sensing can be achieved.

The present invention [9] includes a biosensor including the laminates for biosensor of any one of [1] to [8]; and an electronic component that is electrically connected to the probe, and mounted on the substrate layer.

With this biosensor, the laminate for biosensor described above is included, and therefore increase in impedance and impedance variation of the biosensor can be suppressed.

Effects of the Invention

The laminate for biosensor and biosensor of the present invention can suppress increase and variation in electrode impedance of the biosensor.

BRIEF DESCRIPTION OF THE DRAWINGS

FIG. 2A and FIG. 2B are cross sectional views of the laminate for biosensor shown in FIG. 1: FIG. 2A showing a cross sectional view along A-A; and FIG. 2B showing a cross sectional view along B-B.

FIG. 4A illustrating a step of preparing a substrate layer and a wire; FIG. 4B illustrating a step of bonding a pressure-sensitive adhesive layer and a substrate layer; FIG. 4C illustrating a step of forming an opening, and preparing a probe member step; and FIG. 4D illustrating a step of inserting the probe member to the opening, and forming a connecter.

FIG. 5A illustrating a cross sectional view; and FIG. 5B illustrating a bottom view.

FIG. 11A to FIG. 11E are a process diagram for production of the laminate for biosensor shown in FIG. 9: FIG. 11A illustrating a step of preparing a substrate layer and a wire; FIG. 11B illustrating a step of bonding a pressure-sensitive adhesive layer and a substrate layer; FIG. 11C illustrating a step of forming an opening, and preparing a probe member; FIG. 11D illustrating a step of inserting the probe member to the opening, and forming a connecter; and FIG. 11E illustrating a step of disposing a second pressure-sensitive adhesive layer and a moisture barrier layer.

FIG. 12A illustrating a cross sectional view; and FIG. 12B illustrating a bottom view.

FIG. 16A illustrating a step of preparing a probe sheet; FIG. 16B illustrating a step of disposing a moisture barrier layer on the probe sheet; FIG. 16C illustrating a step of disposing a pressure-sensitive adhesive layer on the moisture barrier layer; FIG. 16D illustrating a step of disposing the substrate layer on the pressure-sensitive adhesive layer; and FIG. 16E illustrating a step of connecting a measurement sample with a lead, and bonding the measurement sample with pig skin.

FIG. 17A being a cross sectional view in Example 2; and FIG. 17B being a cross sectional view in Example 3.

FIG. 18A illustrating a step of preparing a probe sheet; FIG. 18B illustrating a step of disposing a pressure-sensitive adhesive layer on the probe sheet; FIG. 18C illustrating a step of disposing a substrate layer on the pressure-sensitive adhesive layer; FIG. 18D illustrating a step of disposing the moisture barrier layer and second pressure-sensitive adhesive layer on the substrate layer; and FIG. 18E illustrating a step of connecting the measurement sample with a lead, and bonding the measurement sample with pig skin.

DESCRIPTION OF THE EMBODIMENTS

Figure 1:
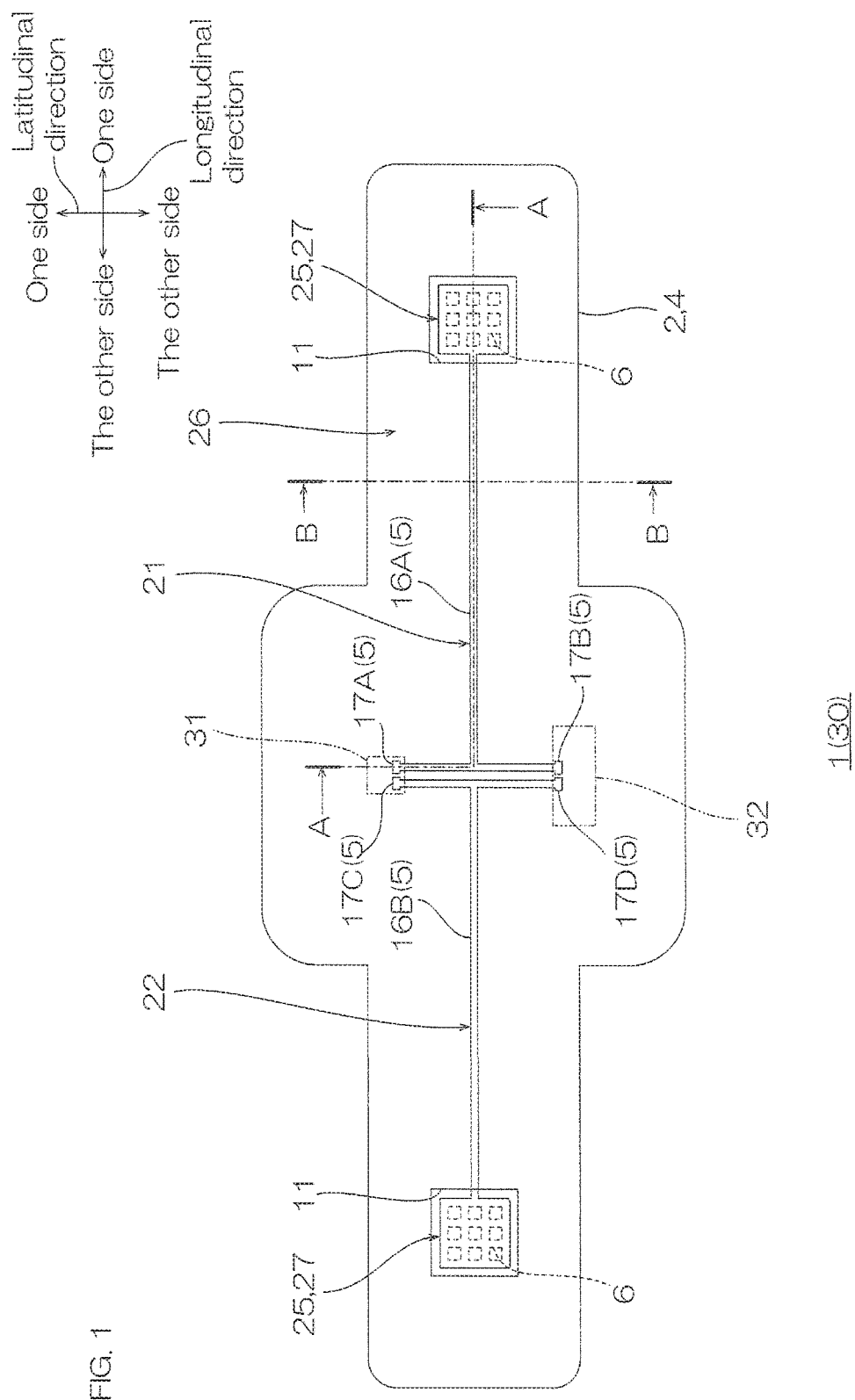
FIG. 1 shows a plan view of the laminate for biosensor of the present invention in a first embodiment.

In FIG. 1, left-right direction on the sheet is longitudinal direction (first direction) of the biosensor laminate 1, laminate for biosensor. Right side on the sheet is longitudinal one side (one side in first direction), left side on the sheet is longitudinal other side (the other side in first direction).

In FIG. 1, up-down direction on the sheet is a latitudinal direction (direction orthogonal to longitudinal direction, width direction, second direction orthogonal to first direction) of the biosensor laminate 1. Upper side on the sheet is one side in latitudinal direction (one side in width direction, one side in second direction), and lower side on the sheet is the other side in latitudinal direction (the other side in width direction, the other side in second direction).

In FIG. 1, paper thickness direction on the sheet is up-down direction (thickness direction, third direction orthogonal to first direction and second direction) of the biosensor laminate 1. Near side on the sheet is upper side (one side in thickness direction, one side in third direction), and far side on the sheet is lower side (the other side in thickness direction, the other side in third direction). The directions are in accordance with the direction arrows described in the figures.

These definitions of the directions are not intended to limit the orientations of the biosensor laminate 1 and wearable electrocardiograph 30 (described later) at the time of production and use.

First Embodiment

A first embodiment of the laminate for biosensor of the present invention is described with reference to FIG. 1 to FIG. 8.

As shown in FIG. 1 to FIG. 4D, a biosensor laminate 1, laminate for biosensor, in one embodiment of the first embodiment has generally a flat plate shape extending in longitudinal direction. The biosensor laminate 1 includes a pressure-sensitive adhesive layer 2, a moisture barrier layer 3, a substrate layer 4, a wire layer 5, a probe 6, and a connecter 7. To be specific, the biosensor laminate 1 includes a pressure-sensitive adhesive layer 2, a moisture barrier layer 3 disposed inside the pressure-sensitive adhesive layer 2, a substrate layer 4 disposed at the upper side of the pressure-sensitive adhesive layer 2 and moisture barrier layer 3, a wire layer 5 embedded in the substrate layer 4, a probe 6 embedded in the moisture barrier layer 3, and a connecter 7 that electrically connects the wire layer 5 and the probe 6.

(Pressure-Sensitive Adhesive Layer)

The pressure-sensitive adhesive layer 2 is a layer that gives pressure-sensitive adhesiveness to the lower face of the biosensor laminate 1 for attaching the lower face of the biosensor laminate 1 to the surface, such as skin 33, of a living body.

The pressure-sensitive adhesive layer 2 forms, as shown in FIG. 1 to FIG. 2B, along with the moisture barrier layer 3 and probe 6 to be described later, the lower face of the biosensor laminate 1. The pressure-sensitive adhesive layer 2 forms the contour of the part of biosensor laminate 1. The pressure-sensitive adhesive layer 2 has a flat plate shape (sheet shape) extending in longitudinal direction. To be specific, the pressure-sensitive adhesive layer 2 has, for example, a band shape extending in longitudinal direction, with a longitudinal center portion bulging toward latitudinal both outsides. In the pressure-sensitive adhesive layer 2, both end edges in latitudinal direction of the longitudinal center portion are positioned at latitudinal both outsides relative to the both end edges in latitudinal direction of other than the longitudinal center portion.

The pressure-sensitive adhesive layer 2 has an adhesion opening 11 at each of the both end portions, in longitudinal direction, of the layer 2. The two adhesion openings 11 each has a generally rectangular shape (square shape) in plan view, and penetrates the pressure-sensitive adhesive layer 2 in the thickness direction. The moisture barrier layer 3 and the connecter 7 (described later) are disposed in the adhesion opening 11.

The pressure-sensitive adhesive layer 2 has a moisture permeability of, for example, 1000 g/m²·day or more, preferably 1500 g/m²·day or more, and for example, 10000 g/m²·day or less. When the pressure-sensitive adhesive layer 2 has a moisture permeability of the above-described lower limit or more, when the biosensor laminate 1 is attached to a living body, the sweat generated from the living body can appropriately permeate through the layer 2 to the outside of the biosensor laminate 1 to reduce uncomfortableness (steaming, etc.) felt by the living body. Therefore, it has excellent wearability.

In the present invention, the moisture permeability of layers such as the pressure-sensitive adhesive layer 2 is calculated based on the following steps.

(1) A weighing bottle having an opening of predetermined area S is prepared, and sufficient water is poured in the weighing bottle (liquid surface should be below the opening).

(2) A measurement sample (pressure-sensitive adhesive layer 2, etc.) is disposed at the opening so that the opening of the weighing bottle is close and tension is not generated in the measurement sample, whereby the measurement sample is fixed in the weighing bottle and the weighing bottle is sealed tight.

(3) The total mass $M_1$ of the measurement sample, water, and weighing bottle immediately after the sealing was measured.

(4) The weighing bottle sealed tight is allowed to stand under conditions of 40° C. and 30% RH for 24 hours.

(5) The total mass $M_2$ of the measurement sample, water, and weighing bottle after they were allowed to stand for 24 hours was measured.

(6) The moisture permeability P was calculated with formula $[P=(M_1-M_2)/S]$.

The materials for the pressure-sensitive adhesive layer 2 are those materials having pressure-sensitive adhesiveness, and, preferably, also having biocompatibility. Examples of such a material include acrylic pressure-sensitive adhesive, and silicone pressure-sensitive adhesive, and preferably, acrylic pressure-sensitive adhesive is used.

The acrylic pressure-sensitive adhesive (acrylic pressure-sensitive adhesive composition) contains acrylic polymer.

The acrylic polymer is a main component of the acrylic pressure-sensitive adhesive, and is a pressure-sensitive adhesive component.

The acrylic polymer is a polymer produced by polymerizing monomer components containing (meth)acrylic ester (to be specific, acrylic acid isononyl, acrylic acid methoxy ethyl, etc.) as a main component (content 70 mass % or more, 99 mass % or less in the monomer components), and other monomer (to be specific, acrylic acid, etc.) that is copolymerizable with (meth)acrylic ester as an optional component (content 30 mass % or less, 1 mass % or more in the monomer components). Examples of the acrylic polymer include acrylic polymer described in Japanese Unexamined Patent Publication No. 2003-342541.

The acrylic pressure-sensitive adhesive preferably further contains carboxylic acid ester.

Carboxylic acid ester in the acrylic pressure-sensitive adhesive is a pressure-sensitive adhesive strength adjustor that reduces the pressure-sensitive adhesive strength of the acrylic polymer, and adjusts the pressure-sensitive adhesive strength of the pressure-sensitive adhesive layer 2. Carboxylic acid ester is carboxylic acid ester miscible with acrylic polymer.

Examples of the carboxylic acid ester include ester of carboxylic acid (fatty acid) with trihydric alcohol, such as capric triglyceride, capric monoglyceride, tri-2-ethyl hexanoic acid glyceryl, tri capric acid glyceryl, tri lauric acid glyceryl, glyceryl triisostearate, tri oleic acid glyceryl, and tri-2-ethyl hexanoic acid trimethylolpropane; ester of carboxylic acid with dihydric alcohol, such as propylene glycol dicaprylate, propylene glycol dicaprate, and propylene glycol diisostearate; and ester of carboxylic acid with monohydric alcohol, such as myristic acid ethyl, myristic acid isopropyl, palmitic acid isopropyl, stearic acid butyl, isostearic acid isopropyl, lauric acid hexyl, phthalic acid diethyl, dioctyl phthalate, myristic acid stearyl, oleic acid stearyl, cetyl dimethyl octanoate, cetyl 2-ethyl hexanoate, isocetyl 2-ethyl hexanoate, 2-ethyl hexanoic acid stearyl, and succinic acid dioctyl. Examples of carboxylic acid ester further include cetyl lactate and myristyl lactate. These carboxylic acid esters can be used singly, or can be used in combination.

For the carboxylic acid ester, preferably, an ester of fatty acid and trihydric alcohol is used, more preferably, in view of compatibility, an ester of fatty acid and glycerine is used, even more preferably, capric triglyceride is used.

The carboxylic acid ester content relative to 100 parts by mass of acrylic polymer is, for example, 30 parts by mass or more, preferably 50 parts by mass or more, and for example, 100 parts by mass or less, preferably 70 parts by mass or less.

The acrylic pressure-sensitive adhesive can contain, as necessary, a cross-linking agent. The cross-linking agent is a crosslinking component that crosslinks acrylic polymer. Examples of the cross-linking agent include a polyisocyanate compound, epoxy compound, melamine compound, peroxide compound, urea compound, metal alkoxide compound, metal chelate compound, metal salt compound, carbodiimide compound, oxazoline compound, aziridine compound, and amine compound. These cross-linking agents can be used singly, or can be used in combination. For the cross-linking agent, preferably, a polyisocyanate compound (polyfunctional isocyanate compound) is used.

The cross-linking agent content relative to 100 parts by mass of acrylic polymer is, for example, 0.001 parts by mass or more, preferably 0.01 parts by mass or more, and for example, 10 parts by mass or less, preferably 1 part by mass or less.

The pressure-sensitive adhesive layer 2 has a thickness (excluding the region of adhesion groove 10) of, for example, 10 μm or more, preferably 20 μm or more, and for example, 300 μm or less, preferably 100 μm or less, more preferably 50 μm or less.

(Moisture Barrier Layer)

The moisture barrier layer 3 is a barrier layer that suppresses moisture present surrounding the probe 6 to be described later to permeate the biosensor laminate 1 in the thickness direction. In this manner, moisture is kept at the interface between the lower face of the probe 6 and the skin 33 of a living body.

Figure 3:
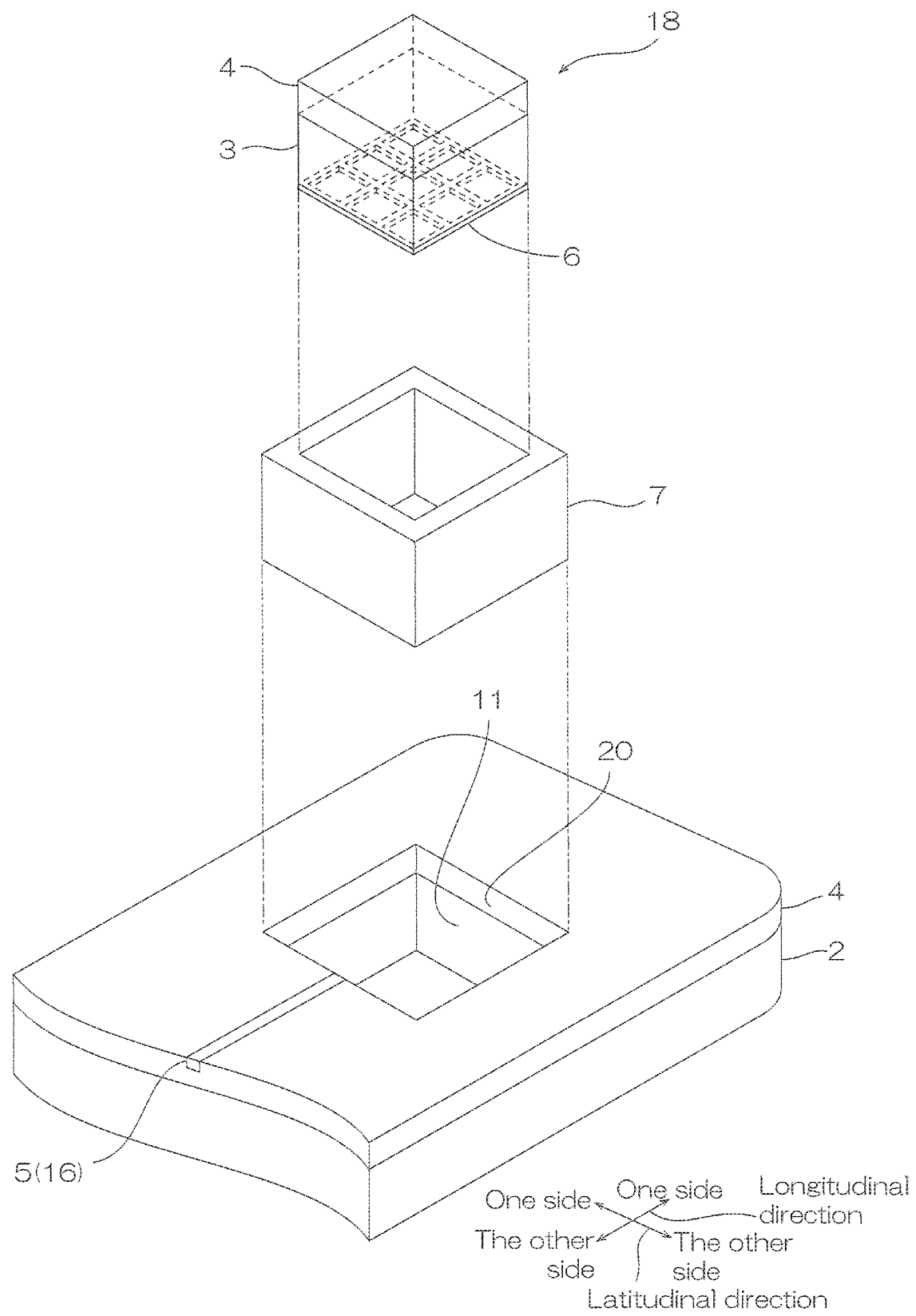
FIG. 3 shows an exploded perspective view of the probe and its surroundings of the laminate for biosensor shown in FIG. 2A.

The moisture barrier layer 3 forms, as shown in FIGS. 1 to 3, the lower face of the biosensor laminate 1 along with the pressure-sensitive adhesive layer 2. The moisture barrier layer 3 has, in plan view, a generally rectangular shape slightly smaller than the adhesion opening 11, and has a flat plate shape (sheet shape).

The moisture barrier layer 3 is disposed inside the adhesion opening 11 of the pressure-sensitive adhesive layer 2. The peripheral face of the moisture barrier layer 3 is, over the entire circumference, in spaced apart relation with the inner periphery of the adhesion opening 11. That is, the pressure-sensitive adhesive layer 2 and the moisture barrier layer 3 define a frame adhesion opening 12 having a generally rectangular frame shape in plan view. The frame adhesion opening 12 is filled with a connecter 7 to be described later.

The moisture barrier layer 3 is disposed so as to overlap with the probe 6 to be described later when projected in the thickness direction. To be specific, the moisture barrier layer 3 is disposed so that the contour of the moisture barrier layer 3 is coincide with the contour of the probe 6 (also with the inner shape of the connecter 7) when projected in the thickness direction. That is, the contour of the moisture barrier layer 3 is the same as the contour of the probe 6 in plan view. The moisture barrier layer 3 is disposed above the probe 6. The lower face of the moisture barrier layer 3 has an adhesion groove 10 corresponding to the probe 6 (described later), and the probe 6 is embedded in the moisture barrier layer 3 at the adhesion groove 10. In this manner, the moisture barrier layer 3 makes contact with the substrate layer 4, probe 6, and connecter 7.

The moisture barrier layer 3 has a moisture permeability lower than the moisture permeability of the pressure-sensitive adhesive layer 2 and substrate layer 4. To be specific, the moisture barrier layer 3 has a moisture permeability of, for example, below 1000 g/m²·day, preferably 600 g/m²·day or less, more preferably 300 g/m²·day or less, even more preferably 80 g/m²·day or less, and for example, 0.001 g/m²·day or more.

For the material of the moisture barrier layer 3, for example, resin is used. To be specific, examples of the moisture barrier layer 3 include resin layers such as a rubber resin layer (polyisobutylene resin layer, butyl rubber resin layer, SBR resin layer, natural rubber/SBR resin layer, etc.), polystyrene resin layer, polyolefin resin layer (polypropylene resin layer, polyethylene resin layer, etc.), acrylic resin layer, and poly vinyl alcohol resin layer. These resin layers can be used singly, or can be used in combination of two or more.

The moisture barrier layer 3 can include, for example, foam. That is, the resin layer can be a resin foam layer such as a polypropylene foam layer and acrylic foam layer.

Preferably, the moisture barrier layer 3 has pressure-sensitive adhesiveness. For the moisture barrier layer of the pressure-sensitive adhesiveness, preferably, a rubber resin layer (rubber pressure-sensitive adhesive layer), more preferably, a polyisobutylene resin layer (polyisobutylene pressure-sensitive adhesive layer) is used.

The polyisobutylene resin layer is formed from a polyisobutylene composition. The polyisobutylene composition contains, as a rubber component, polyisobutylene. The polyisobutylene composition has a polyisobutylene content of, for example, 10 mass % or more, preferably 20 mass % or more, and for example, 50 mass % or less, preferably 40 mass % or less.

The polyisobutylene composition preferably contains a superabsorbent polymer and tackifier. In this manner, excellent moisture barrier properties and pressure-sensitive adhesiveness can be given to the rubber composition such as a polyisobutylene composition.

Examples of the superabsorbent polymer include maleic anhydride salt resin (for example, crosslinked sodium salt of isobutylene-maleic anhydride copolymer, etc.), polyacrylate resin, polysulfonate resin, poly acrylamide resin, and poly vinyl alcohol resin; and preferably, maleic anhydride salt resin is used. The superabsorbent polymer content relative to 100 parts by mass of polyisobutylene is, for example, 1 part by mass or more, preferably 3 parts by mass or more, and for example, 10 parts by mass or less, preferably 5 parts by mass or less.

Examples of the tackifier include rosin resin, terpene resin (for example, terpene-aromatic liquid resin, etc.), coumarone-indene resin, phenol resin, phenol-formaldehyde resin, xylene formalin resin, and petroleum resin (for example, C5 petroleum resin, C9 petroleum resin, C5/C9 petroleum resin, etc.), and preferably, petroleum resin is used. The tackifier content relative to 100 parts by mass of polyisobutylene is, for example, 10 parts by mass or more, preferably 50 parts by mass or more, and for example, 200 parts by mass or less, preferably 150 parts by mass or less.

The polyisobutylene composition further contains, as necessary, a softener, filler, and cross-linking agent.

Examples of the softener include liquid rubber such as polybutene, liquid isoprene rubber, and liquid butadiene rubber; oils such as paraffin oil and naphthene oil; and esters such as phthalic acid ester and phosphoric acid ester, and preferably, liquid rubber is used. The softener content relative to 100 parts by mass of polyisobutylene is, for example, 10 parts by mass or more, preferably 50 parts by mass or more, and for example, 200 parts by mass or less, preferably 150 parts by mass or less.

Examples of the filler include calcium carbonate (for example, calcium carbonate heavy, calcium carbonate light, and Hakuenka), carbon black, talc, mica, clay, mica powder, bentonite, silica, alumina, aluminum silicate, titanium oxide, metal powder (for example, aluminum powder, iron powder, etc.), resin powder (for example, acrylic resin powder, styrene resin powder, etc.), glass powder, boron nitride powder, and metalhydroxide (for example, aluminum hydroxide, magnesium hydroxide, etc.); and preferably, calcium carbonate is used. The filler content relative to 100 parts by mass of polyisobutylene is, for example, 10 parts by mass or more, preferably 50 parts by mass or more, and for example, 200 parts by mass or less, preferably 150 parts by mass or less.

Examples of the cross-linking agent include isocyanate compounds such as hexamethylene diisocyanate. The cross-linking agent content relative to 100 parts by mass of polyisobutylene is, for example, 1 part by mass or more, preferably 3 parts by mass or more, and for example, 10 parts by mass or less, preferably 5 parts by mass or less.

The polyisobutylene composition may also contain known additives such as a foaming agent and a plasticizer at a suitable ratio.

Of those examples of the rubber resin layer (rubber pressure-sensitive adhesive layer), in view of stable attachment to the skin, preferably, the SBR resin layer, natural rubber-SBR resin layer are used, and more preferably, the SBR resin layer is used.

The SBR resin layer is formed from a styrene-butadiene rubber (SBR) composition. The SBR composition contains SBR as a rubber component. The SBR composition has an SBR content of, for example, 10 mass % or more, preferably 20 mass % or more, and for example, 50 mass % or less, preferably 40 mass % or less.

The SBR composition may also contain a superabsorbent polymer, tackifier, softener, filler, and cross-linking agent, as in the case with the polyisobutylene composition.

The natural rubber-SBR resin layer is formed from a natural rubber/SBR composition. The natural rubber-SBR composition contains natural rubber and SBR as a rubber component. In the natural rubber-SBR composition, the natural rubber and SBR contents in total is, for example, 10 mass % or more, preferably 20 mass % or more, and for example, 50 mass % or less, preferably 40 mass % or less.

The natural rubber-SBR composition may also contain a superabsorbent polymer, tackifier, softener, filler, and cross-linking agent, as in the case with the polyisobutylene composition.

The moisture barrier layer 3 has a thickness that is substantially the same as the thickness of the pressure-sensitive adhesive layer 2. To be specific, the moisture barrier layer 3 has a thickness of, for example, 10 μm or more, preferably 20 μm or more, and for example, 300 μm or less, preferably 100 μm or less, more preferably 50 μm or less.

When the biosensor laminate 1 is projected in the thickness direction, the region where the moisture barrier layer 3 is present is referred to as a barrier region 25, and the region other than the barrier region 25 is referred to as a non-barrier region 26. That is, the biosensor laminate 1 includes two barrier regions 25 disposed at both sides in longitudinal direction, and one continuous non-barrier region 26.

The barrier region 25 is smaller than the non-barrier region 26. To be specific, the ratio (A2/A1) of area A2 of the non-barrier region 26 relative to the area A1 of the barrier region 25 is, for example, 2 or more, preferably 5 or more, more preferably 10 or more, and for example, 100 or less. The barrier regions 25 have an area A1 of, for example, 0.1 $cm^2$ or more, preferably 0.5 $cm^2$ or more, more preferably 1 $cm^2$ or more, and for example, 15 $cm^2$ or less, preferably 8 $cm^2$ or less, more preferably 3 $cm^2$ or less. When the above-described ratio is the above-described lower limit or more, or the area of the barrier region 25 is the above-described upper limit or less, the area ratio of the non-barrier region 26 can be increased, and wearability of the biosensor laminate 1 will be more excellent.

(Substrate Layer)

The substrate layer 4 is a support layer that supports the pressure-sensitive adhesive layer 2 and moisture barrier layer 3.

The substrate layer 4 forms the upper face of the biosensor laminate 1, as shown in FIG. 1 to FIG. 2B. The substrate layer 4 forms the contour of the biosensor laminate 1 along with the pressure-sensitive adhesive layer 2. The contour of the substrate layer 4 in plan view is the same as the contour of the pressure-sensitive adhesive layer 2 in plan view. The substrate layer 4 is disposed at the entire upper face of the pressure-sensitive adhesive layer 2 and moisture barrier layer 3. The substrate layer 4 has a sheet shape extending in longitudinal direction.

On the upper face of the substrate layer 4, as shown in FIGS. 2A to 2B, a substrate groove 14 corresponding to the wire layer 5 is formed. The substrate groove 14 has the same pattern shape as the wire layer 5 in plan view. The substrate groove 14 is opened upward.

The substrate layer 4 has a frame substrate opening 15 corresponding to the frame adhesion opening 12. The frame substrate opening 15 communicates with the frame adhesion opening 12 in the thickness direction. The frame substrate opening 15 has a generally rectangular frame shape, in plan view, having the same shape and size as that of the frame adhesion opening 12.

The substrate layer 4 has a moisture permeability of, for example, 1000 g/m$^2$·day or more, preferably 2000 g/m$^2$·day or more, and for example, 10000 g/m$^2$·day or less. When the substrate layer 4 has a moisture permeability of the above-described lower limit or more, when the biosensor laminate 1 is attached to a living body, sweat generated by the living body is allowed to appropriately permeate through the biosensor laminate 1 to the outside, and uncomfortableness (steaming, etc.) felt by the living body can be decreased. Therefore, it has excellent wearability.

The substrate layer 4 has an elongation at break of, for example, 100% or more, preferably 200% or more, more preferably 300% or more, and for example, 2000% or less. The elongation at break is measured based on JIS K 7127 (1999), with a tensile speed of 5 mm/min and a test piece type 2.

The substrate layer 4 has a tensile strength at 20° C. (between chucks 100 mm, tensile speed 300 mm/min, strength at break) of, for example, 0.1 N/20 mm or more, preferably 1 N/20 mm or more, and for example, 20 N/20 mm or less. The tensile strength is measured based on JIS K 7127(1999).

The substrate layer 4 has a tensile storage modulus E at 20° C. of, for example, 2000 MPa or less, preferably 1000 MPa or less, more preferably 100 MPa or less, even more preferably 50 MPa or less, particularly preferably 20 MPa or less, and for example, 0.1 MPa or more. The tensile storage modulus E' at 20° C. is obtained by subjecting the substrate layer 4 to dynamic viscoelasticity measurement under conditions of a frequency 1 Hz and a temperature increase speed of 10° C./min.

The material of the substrate layer 4 has stretching property when it satisfies at least one, preferably two or more, more preferably all of three of the following conditions: (1) elongation at break is 100% or more, (2) tensile strength is 20 N/20 mm or less, and (3) tensile storage modulus E' is 2000 MPa or less.

The substrate layer 4 is formed from a substrate composition. The substrate composition contains a substrate resin.

The substrate resin is a main component of the substrate composition, and for example, it is a flexibility resin that gives the substrate layer 4 appropriate stretching property, flexibility, and tenacity.

Examples of the substrate resin include thermoplastic resin such as polyurethane resin, silicone resin, polystyrene resin, vinyl chloride resin, and polyester resin. Preferably, polyurethane resin is used. In this manner, the substrate layer 4 can have more excellent stretching property.

The substrate composition (substrate layer 4) has a substrate resin content of, for example, 70 mass % or more, preferably 80 mass % or more, and for example, 99 mass % or less, preferably 95 mass % or less.

The substrate composition further contains, preferably, carboxylic acid ester. Carboxylic acid ester in the substrate composition is an elasticity modifier that gives flexibility to the biosensor laminate 1.

To be specific, those carboxylic acid esters given as examples for the pressure-sensitive adhesive of the pressure-sensitive adhesive layer 2 can be used, and preferably, tri fatty acid glyceryl is used.

The carboxylic acid ester content relative to 100 parts by mass of the substrate resin is, for example, 10 parts by mass or more, preferably 30 parts by mass or more, and for example, 80 parts by mass or less, preferably 70 parts by mass or less. The substrate composition (substrate layer 4) has a carboxylic acid ester content of, for example, 10 mass % or more, preferably 25 mass % or more, and for example, 45 mass % or less, preferably 35 mass % or less.

The substrate layer 4 has a thickness (excluding the region of the substrate groove 14) of, for example, 1 μm or more, preferably 5 μm or more, and for example, 300 μm or less, preferably 100 μm or less, preferably 50 μm or less. When the substrate layer 4 has a thickness of the above-described lower limit or more, the substrate layer 4 can reliably keep its shape, and therefore handleability of the biosensor laminate 1 is excellent. When the substrate layer 4 has a thickness of the above-described upper limit or less, the substrate layer 4 can be attached to the living body reliably.

(Wire Layer)

As shown in FIG. 2A to FIG. 3, the wire layer 5 is embedded in the substrate groove 14 of the substrate layer 4. To be specific, the wire layer 5 is embedded in the upper end portion of the substrate layer 4 so as to be exposed from the upper face of the substrate layer 4. The entire lower face and the entire side face of the wire layer 5 is in contact with the substrate layer 4. The upper face of the wire layer 5 is exposed from the upper face (excluding the substrate groove 14) of the substrate layer 4. The upper face of the wire layer 5 forms the upper face of the biosensor laminate 1 along with the upper face of the substrate layer 4, and the upper face of the wire layer 5 is flush with the upper face of the substrate layer 4.

As shown in FIG. 1, the wire layer 5 has a wire pattern connecting the connecter 7 with the electronic component 31 (described later) and battery 32 (described later). To be specific, the wire layer 5 includes a first wire pattern 21 and a second wire pattern 22 independently.

The first wire pattern 21 is disposed at one side in longitudinal direction of the substrate layer 4. The first wire pattern 21 includes a first wire 16A and a first terminal 17A and a second terminal 17B continuous thereto.

The first wire pattern 21 has generally a T-shape in plan view. To be specific, the first wire pattern 21 extends from longitudinal one end portion of the substrate layer 4 to longitudinal other side, and branches out at a center portion in the longitudinal direction of the substrate layer 4 and extends toward both outsides in latitudinal direction.

The first terminal 17A and the second terminal 17B are disposed at latitudinal both end portions at a center portion in the longitudinal direction of the substrate layer 4. The first terminal 17A and the second terminal 17B each has a substantially rectangular shape in plan view (land shape). The first terminal 17A and the second terminal 17B is each continuous with one of the both end portions of the first wire 16A extending toward both outside in the latitudinal direction at a center portion in the longitudinal direction of the substrate layer 4.

The second wire pattern 22 is provided at the other side in the longitudinal direction of the first wire pattern 21 in spaced apart relation. The second wire pattern 22 includes a second wire 16B and a third terminal 17C and a fourth terminal 17D continuous thereto.

The second wire pattern 22 has a generally T-shape in plan view. To be specific, the second wire pattern 22 extends from the other end portion in the longitudinal direction of the substrate layer 4 toward one side in longitudinal direction, branches out at a center portion in the longitudinal direction of the substrate layer 4 and extend toward both outside in the latitudinal direction.

The third terminal 17C and fourth terminal 17D are disposed at latitudinal both end portions at a center portion in the longitudinal direction of the substrate layer 4. The third terminal 17C and the fourth terminal 17D each has a substantially rectangular shape in plan view (land shape). The third terminal 17C and the fourth terminal 17D is each continuous with one of the both end portions of the second wire 16B extending toward both outsides in the latitudinal direction at a center portion in the longitudinal direction of the substrate layer 4.

For the material of the wire layer 5, for example, metal conductors such as copper, nickel, gold, and alloys thereof are used, and preferably, copper is used.

The wire layer 5 has a thickness of, for example, 0.1 μm or more, preferably 1 μm or more, and for example, less than 100 μm, preferably 50 μm or less, more preferably 5 μm or less.

(Probe)

The probe 6 is an electrode that detects a signal or signals, such as electric signals, temperatures, vibrations, sweat, and metabolites, of a living body when the pressure-sensitive adhesive layer 2 is attached to the surface of a living body, making contact with the surface of the living body.

As shown in FIG. 2 A to FIG. 3, the probe 6 is embedded in the adhesion groove 10 of the moisture barrier layer 3. To be specific, the probe 6 is embedded in the lower end portion of the moisture barrier layer 3 so as to be exposed from the lower face of the moisture barrier layer 3 inside the connecter 7. The entire upper face and the entire side face of the probe 6 are in contact with the moisture barrier layer 3. The lower face of the probe 6 is exposed at the lower face of the moisture barrier layer 3 (excluding the adhesion groove 10). The lower face of the probe 6 forms the lower face of the biosensor laminate 1 along with the lower face of the moisture barrier layer 3 and pressure-sensitive adhesive layer 2, and the lower face of the probe 6 is flush with the lower face of the moisture barrier layer 3.

The probe 6 has a shape that includes an exposure region 13 that allows the moisture barrier layer 13 to be exposed at the lower face of the biosensor laminate 1. The probe 6 has, for example, a mesh shape in plan view. To be specific, the contour of the probe 6 (that is, inner shape of the connecter 7) has a generally rectangular shape in plan view, and the inner side of the probe 6 has a grid shape in plan view. The lower face of the moisture barrier layer 13 is exposed at the gaps of the grid shape in plan view (exposure region 13).

Examples of the material of the probe 6 include an electrically conductive resin composition, and metal conductors given as examples for the wire layer 5; and preferably, an electrically conductive resin composition is used.

The electrically conductive resin composition contains, for example, electrically conductive polymers and resin components.

Examples of the electrically conductive polymer include polyaniline, polypyrrole, polythiophene, poly (ethylenedioxythiophene) (PEDOT), poly (ethylenedioxythiophene)-polystyrene sulfonate (PEDOT-PSS).

Examples of the resin component include poly vinyl alcohol resin, polyester resin, polyurethane resin, acrylic resin, vinyl resin, epoxy resin, and amide resin.

Known additives such as a cross-linking agent, plasticizer, and surfactant may be contained in the resin component other than the above-described resin.

The electrically conductive polymer content relative to 100 parts by mass of the resin component is, for example, 1 part by mass or more, preferably 5 parts by mass or more, and for example, 50 parts by mass or less, preferably 20 parts by mass or less.

For the method for forming a probe 6 using the electrically conductive resin composition, the method described in Japanese Unexamined Patent Publication No. 2017-66271 is used.

The area A3 of the probe region 27 is substantially the same as the area A1 of the barrier region 25, to be specific, for example, 0.1 $cm^2$ or more, preferably 0.5 $cm^2$ or more, more preferably 1 $cm^2$ or more, and for example, 15 $cm^2$ or less, preferably 10 $cm^2$ or less, more preferably 8 $cm^2$ or less. The probe region 27 is a region surrounded by the contour of the probe 6 (also the inner periphery of the connecter 7) in plan view.

The probe 6 has a thickness of, for example, 0.1 μm or more, preferably 1 μm or more, and for example, less than 100 μm, preferably 50 μm or less, more preferably 20 μm or less.

(Connecter)

As shown in FIG. 2A to FIG. 3, the connecter 7 is provided in correspondence with the frame substrate opening 15 and the frame adhesion opening 12, and has the same shape as those. The connecter 7 penetrates (passes through) the biosensor laminate 1 in the thickness direction (up-down direction), and fills the frame substrate opening 15 and the frame adhesion opening 12. The connecter 7 has a substantially hollow prism shape with its axis extending in the thickness direction.

The internal face of the connecter 7 is in contact with the probe 6, moisture barrier layer 3, and the substrate layer 4 inside the frame substrate opening 15. The external face of the connecter 7 is in contact with the wire layer 5 (first wire 16A, first wire 16B), pressure-sensitive adhesive layer 2, and the substrate layer 4 outside the frame substrate opening 15. In this manner, the connecter 7 electrically connects the wire layer 5 and probe 6.

For the material of the connecter 7, the above-described metal conductor and electrically conductive resin (including electrically conductive polymer) are used, and preferably, electrically conductive resin is used.

(Method for Producing Laminate for Biosensor)

Next, description is given below of the method for producing a biosensor laminate 1 in one embodiment with reference to FIG. 4A to FIG. 4D.

Figure 4A:
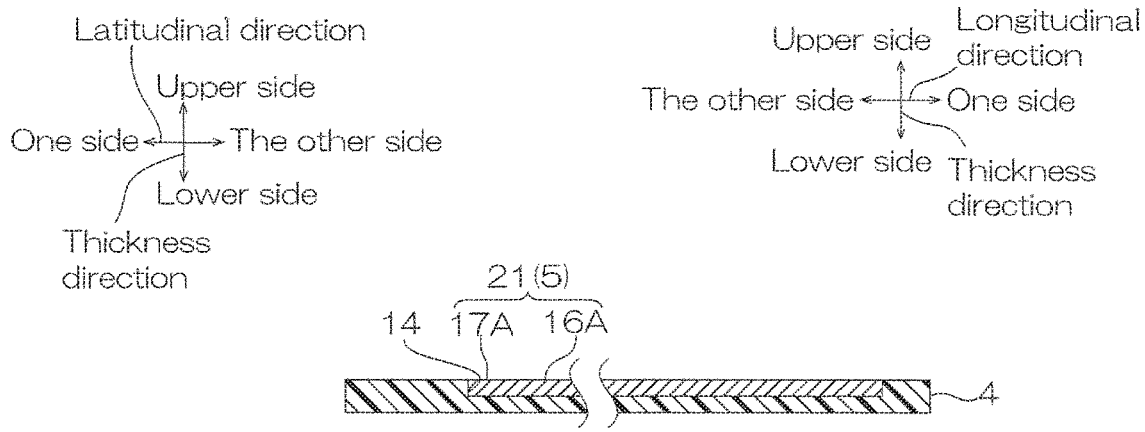
FIG. 4A to FIG. 4D are a process diagram for production of the laminate for biosensor shown in FIG. 2A.

As shown in FIG. 4A, in this method, first, a substrate layer 4 and a wire layer 5 are prepared.

For example, based on the method described in Japanese Unexamined Patent Publication No. 2017-22236 and Japanese Unexamined Patent Publication No. 2017-22237, the substrate layer 4 and the wire layer 5 are prepared so that the wire layer 5 is embedded in the substrate groove 14.

Figure 4B:
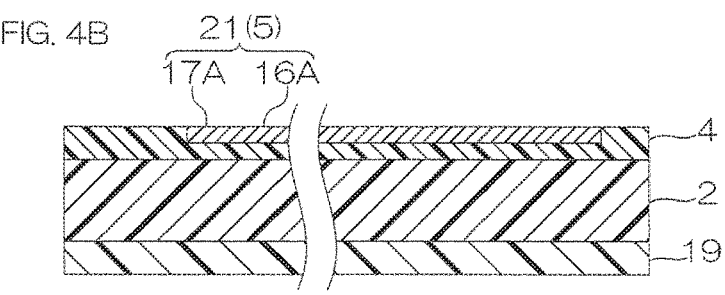

As shown in FIG. 4B, then, the pressure-sensitive adhesive layer 2 is disposed on the lower face of the substrate layer 4.

To dispose the pressure-sensitive adhesive layer 2, for example, first, an application liquid containing a material of the pressure-sensitive adhesive layer 2 (for example, the above-described acrylic pressure-sensitive adhesive) is prepared, and then the application liquid is applied on the upper face of the release sheet 19, and thereafter, it is dried by heating. In this manner, the pressure-sensitive adhesive layer 2 is disposed on the upper face of the release sheet 19. The release sheet 19 has, for example, a sheet shape extending in longitudinal direction. For the material of the release sheet 19, for example, resin such as polyethylene terephthalate is used.

Then, the pressure-sensitive adhesive layer 2 and substrate layer 4 are bonded, for example, with a laminator. To be specific, the upper face of the pressure-sensitive adhesive layer 2 is brought into contact with the lower face of the substrate layer 4.

At this point, the pressure-sensitive adhesive layer 2 and the substrate layer 4 each has no frame adhesion opening 12 and no frame substrate opening 15, respectively.

Figure 4C:
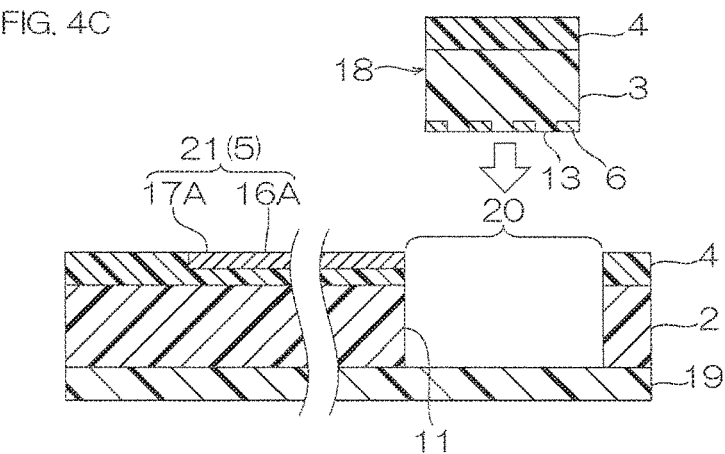

As shown in FIG. 4C, then, the laminate opening 20 is formed in the pressure-sensitive adhesive layer 2 and substrate layer 4.

The laminate opening 20 is in correspondence with the adhesion opening 11, and penetrates the laminate of the pressure-sensitive adhesive layer 2 and substrate layer 4. The laminate opening 20 is a hole (penetration hole) having generally a circular shape in plan view defined by an outer peripheral face defining the adhesion opening 11 and an outer peripheral face defined by the frame substrate opening 15. That is, the laminate opening 20 has the same shape as that of the adhesion opening 11 in plan view. The laminate opening 20 is opened toward the upper side. Meanwhile, the lower end of the laminate opening 20 is closed with the release sheet 19.

To form the laminate opening 20, the pressure-sensitive adhesive layer 2 and the substrate layer 4 are, for example, punched or subjected to half-etching.

Thereafter, the first probe member 18 is prepared, and it is inserted in the laminate opening 20.

As shown in FIG. 3, the first probe member 18 has a generally rectangular shape in plan view. The first probe member 18 includes a probe 6, a moisture barrier layer 3 in which the probe 6 is embedded, and a substrate layer 4 disposed on the upper face of the moisture barrier layer 3.

To prepare the first probe member 18, a probe-containing sheet is prepared, and the probe-containing sheet is trimmed by, for example, punching. The probe-containing sheet is prepared by, for example, producing the moisture barrier layer 3 and the probe 6 embedded in the lower face thereof, and then laminating the substrate layer 4 on the upper face of the moisture barrier layer 3, based on the method described in Japanese Unexamined Patent Publication No. 2017-66271, Japanese Unexamined Patent Publication No. 2017-22236, Japanese Unexamined Patent Publication No. 2017-22237.

Thereafter, as shown in the arrow in FIG. 4C, the first probe member 18 is inserted in the laminate opening 20.

At this time, a space is provided between the first probe member 18 and the surrounding face of the laminate opening 20. That is, the first probe member 18 is inserted in the laminate opening 20 so as to form the frame substrate opening 15 and the frame adhesion opening 12.

Figure 4D:
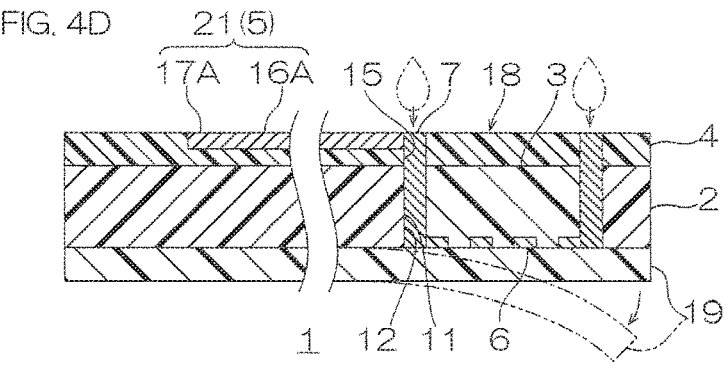

As shown in FIG. 4D, then, the connecter 7 is provided in the frame substrate opening 15 and the frame adhesion opening 12.

When the material of the connecter 7 is electrically conductive resin, the electrically conductive resin is inserted in the frame substrate opening 15 and frame adhesion opening 12. Thereafter, as necessary, the electrically conductive resin is heated.

The biosensor laminate 1 is produced in this manner.

The biosensor laminate 1 produced in this manner includes a pressure-sensitive adhesive layer 2, moisture barrier layer 3, substrate layer 4, wire layer 5, probe 6, connecter 7, and release sheet 19. The biosensor laminate 1 may be composed only of, as shown in FIG. 2A and FIG. 2B, the pressure-sensitive adhesive layer 2, moisture barrier layer 3, substrate layer 4, wire layer 5, probe 6, and connecter 7, without including the release sheet 19.

In the biosensor laminate 1, when it is attached to the skin 33 of a living body, the moisture barrier layer 3 can suppress the moisture present at the interface between the skin 33 of a living body and the probe 6 to permeate through the biosensor laminate 1 in the thickness direction. Therefore, the moisture can be kept uniformly at the lower face of the probe 6, and dryness of the probe 6 can be suppressed uniformly. Therefore, increase and variation in electrode impedance can be suppressed. Furthermore, fixing stability such as adherence and keeping force are excellent.

In the biosensor laminate 1, the moisture barrier layer 3 is disposed inside the pressure-sensitive adhesive layer 2. Therefore, the moisture barrier layer 3 is disposed at a position near the probe 6. Therefore, the moisture can be kept at the lower face of the probe 6 even more reliably.

Figure 14:
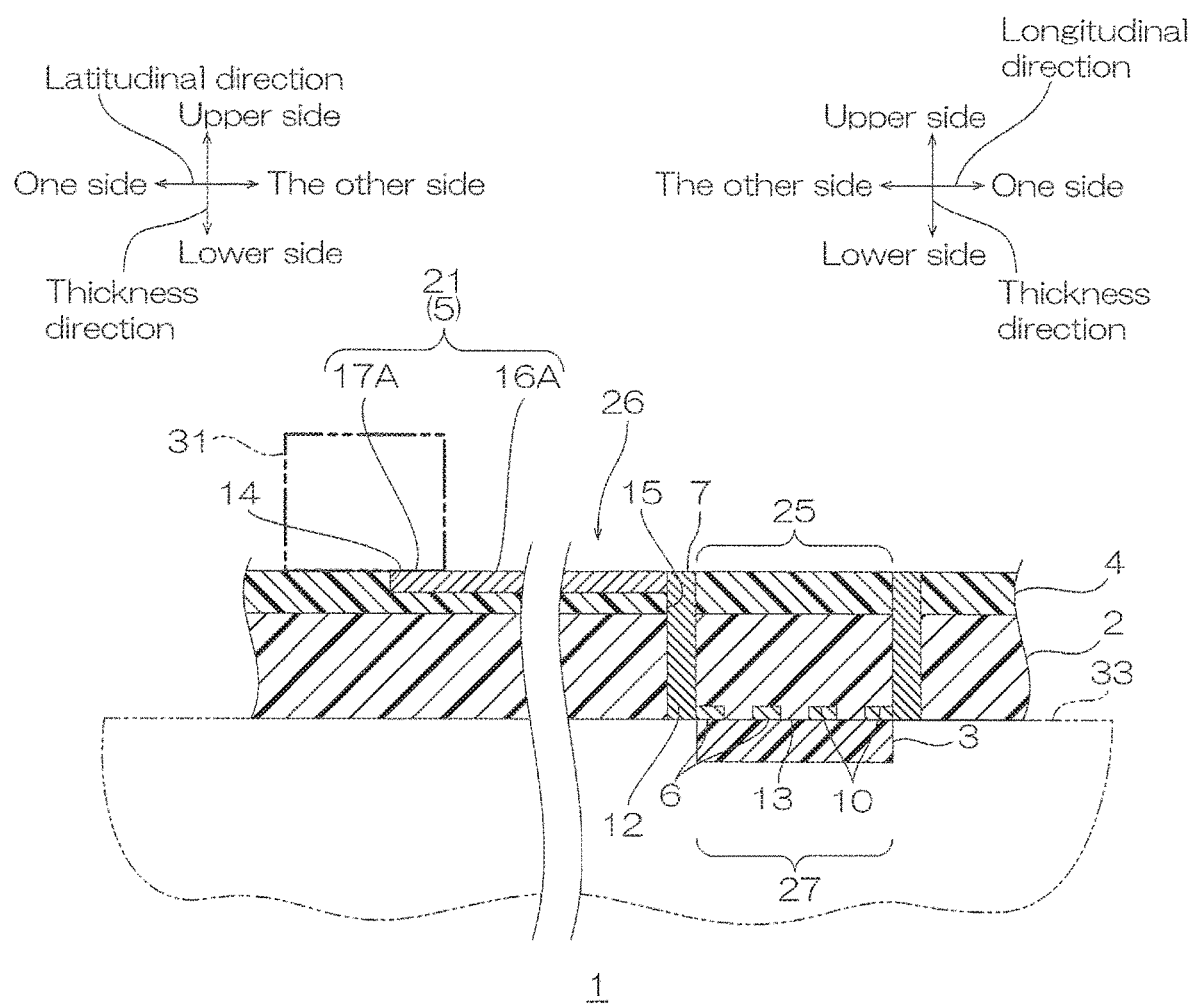
FIG. 14 shows a cross-sectional view of the laminate for biosensor of the present invention in a third embodiment.

Furthermore, in the biosensor laminate 1, the moisture barrier layer 3 is disposed at a side upper than the lower face of the probe. Therefore, compared with the biosensor laminate 1 (third embodiment, ref: FIG. 14) in which the moisture barrier layer 3 is disposed at a lower side than the lower face of the probe 6, the moisture barrier layer 3 does not require electrical conductivity, and the material of the moisture barrier layer 3 can be freely selected, and a material with high moisture barrier properties can be selected.

In the biosensor laminate 1, the moisture barrier layer 3 includes pressure-sensitive adhesiveness. Therefore, the lower face of the moisture barrier layer 3 can be allowed to be exposed at the exposure region 13 (to be specific, gaps of the mesh) of the probe 6, and the lower face of the moisture barrier layer 3 can be allowed to be adhered to the skin 33 of a living body pressure-sensitively. Therefore, the probe 6 can be allowed to contact the skin 33 of a living body uniformly and reliably, and more reliable sensing can be achieved. The moisture barrier layer 3 can be allowed to adhere to the connecter 7, probe 6, and substrate layer 4 pressure-sensitively, and detachment of the moisture barrier layer 3 can be reliably suppressed.

In the biosensor laminate 1, the probe 6 has an exposure region 13 (to be specific, mesh). Thus, the moisture barrier layer 3 (for example, rubber resin layer) with pressure-sensitive adhesiveness can be exposed at the exposure region 13 (to be specific, gaps of the mesh) in the lower face of the biosensor laminate 1. Thus, the entire face of the probe 6 can be brought into contact with the skin 33 of a living body. As a result, more reliable sensing can be achieved.

The biosensor laminate 1 is distributed singly, and is an industrially applicable device. To be specific, the biosensor laminate 1 can be distributed singly, separately from the electronic component 31 and battery 32 (ref: phantom line in FIG. 1) to be described later. That is, in the biosensor laminate 1, the electronic component 31 or battery 32 is not mounted, and it is a component for producing a biosensor such as a wearable electrocardiograph 30.

(Biosensor)

Next, description is given below of a wearable electrocardiograph 30 as an example of a biosensor and a method for using it.

As shown in FIG. 1 and FIGS. 2A to 2B, to produce a wearable electrocardiograph 30 including a biosensor laminate 1, for example, first, the biosensor laminate 1, electronic component 31, and battery 32 are prepared.

Examples of the electronic component 31 include an analog front-end, microcomputer, and memory for processing and storing electric signals from a living body obtained by the probe 6; and a communication IC and transmitter for converting electric signals to electro-magnetic waves and wirelessly transmitting them to an external receiver. The electronic component 31 may include some or all of these. The electronic component 31 has two, or three or more terminals (not shown) provided on the lower face thereof.

The battery 32 has two terminals (not shown) provided at its lower face.

Then, the two terminals of the electronic component 31 are electrically connected with the first terminal 17A and third terminal 17C. The two terminals of the battery 32 are electrically connected with the second terminal 17B and fourth terminal 17D.

In this manner, the wearable electrocardiograph 30 including the biosensor laminate 1, the electronic component 31 and the battery 32 is produced, where the electronic component 31 and the battery 32 are mounted on the biosensor laminate 1.

To use the wearable electrocardiograph 30, first, the release sheet 19 (ref: arrow and phantom line in FIG. 4D) is released from the pressure-sensitive adhesive layer 2 and probe 6.

As shown with the phantom line in FIG. 2A, then, the lower face of the pressure-sensitive adhesive layer 2 is brought into contact with, for example, the skin 33 of a living body. To be specific, the pressure-sensitive adhesive layer 2 is brought into contact with (attached to) the skin 33 puressure-sensitivly. In this manner, the lower face of the probe 6 is brought into contact with the surface of the skin 33.

At this time, the lower face of the probe 6, or the surface of the skin 33 is wetted with water. In this manner, water is inserted at the interface between the lower face of the probe 6 and skin 33.

Then, the probe 6 senses the cardiac action potential as electric signals, and the electric signal sensed acquired by the probe 6 is inputted to the electronic component 31 through the connecter 7 and wire layer 5. The electronic component 31 processes the electric signal based on the electric power supplied from the battery 32, and store that information. Furthermore, as necessary, the electric signals are converted to electro-magnetic waves, and they are wirelessly transmitted to an external receiver.

In the method of using the wearable electrocardiograph 30, the impedance of the probe 6 can be decreased because water which increases electrical conductivity is provided at the interface between the probe 6 and skin 33. Thus, sensing of noise, i.e., other than the cardiac electric signal, can be suppressed.

In the method of using the wearable electrocardiograph 30, the wearable electrocardiograph 30 includes the biosensor laminate 1, and therefore the moisture barrier layer 3 is present in the thickness direction of the probe 6. Thus, the moisture permeation through the biosensor is suppressed, and the drying of the interface is suppressed. Thus, even when it is attached to a living body and used for a long period of time, increase in the impedance of the probe 6 can be suppressed. Furthermore, sufficient water can be present uniformly at the interface, and therefore variation in impedance of the probe 6 can also be suppressed.

Modified Example

In the modified examples below, the members and steps corresponding to those described in the embodiment above are designated by the same reference numerals, and detailed descriptions thereof are omitted. These modified examples can be suitably combined. Furthermore, the modified examples have the same operations and effects as those in the embodiment unless otherwise noted.

First Modified Example

Figure 5A:
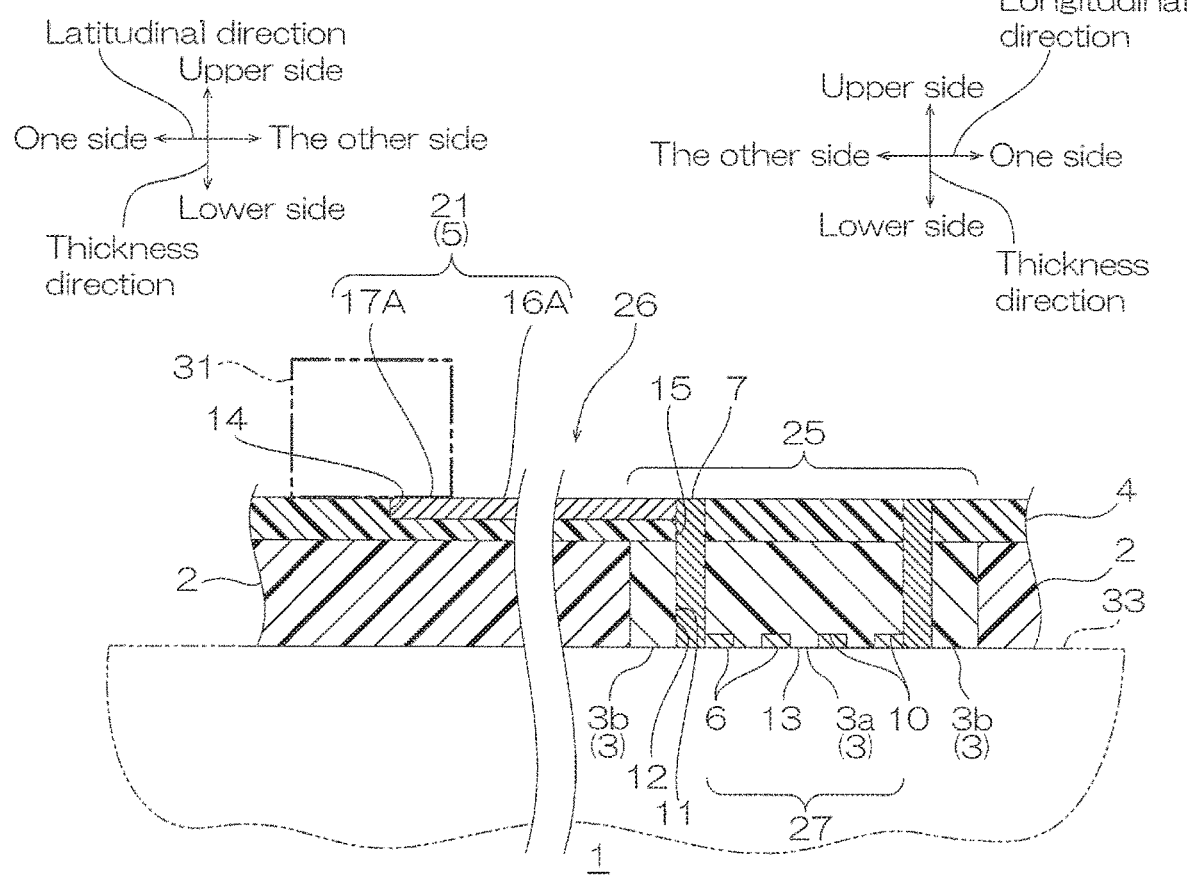
FIG. 5A to FIG. 5B are a modified example of the laminate for biosensor in the first embodiment (embodiment in which the moisture barrier layer is larger than probe)
Figure 5B:
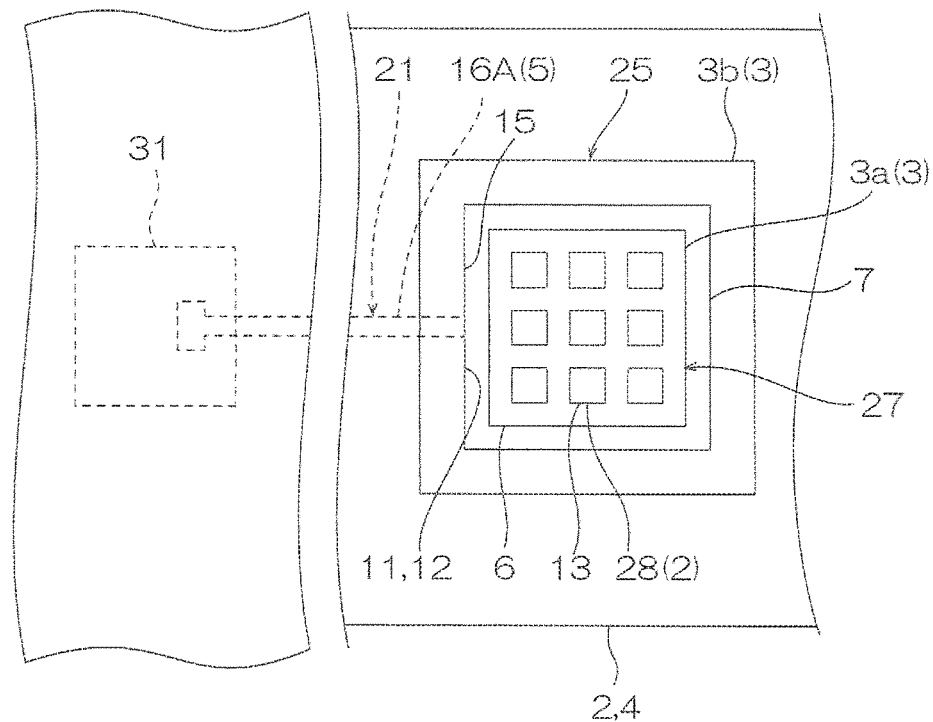

In the embodiment shown in FIG. 1, the contour of the moisture barrier layer 3 coincides with the contour of the probe 6 when projected in the thickness direction, but for example, as shown in FIGS. 5A to 5B, the moisture barrier layer 3 may include the probe 6 when projected in the thickness direction. That is, the contour of the moisture barrier layer 3 may be larger than the contour of the probe 6 in plan view.

In the embodiment shown in FIGS. 5A to 5B, the moisture barrier layer 3 includes an inner barrier layer 3a disposed inside the connecter 7, and an outer barrier layer 3b disposed outside the connecter 7.

The inner barrier layer 3a has a generally rectangular shape in plan view, and its external peripheral face is in contact with the inner periphery of the connecter 7.

The outer barrier layer 3b has a generally rectangular frame shape in plan view, and its inner peripheral face is in contact with the external peripheral face of the connecter 7, and its external peripheral face is in contact with the pressure-sensitive adhesive layer 2.

The barrier region 25 is larger than the probe region 27. To be specific, the ratio of the area A1 of the barrier region 25 relative to the area A3 of the probe region 27 (A1/A3) is, for example, more than 1, preferably 2 or more, more preferably 6 or more, and for example, 20 or less, preferably 15 or less. To be specific, the area A1 of the barrier region 25 is, for example, 1 cm$^2$ or more, preferably 4 cm$^2$ or more, and for example, 20 cm$^2$ or less, preferably 10 cm$^2$ or less. When the area A1 of the barrier region 25 is the above-described lower limit or more, increase and variation in impedance of the probe 6 can be suppressed even more. When the area A1 of the barrier region 25 is the above-described upper limit or less, wearability can be improved even more.

In view of excellent wearability, preferably, the embodiment as shown in FIG. 1 is used. Meanwhile, in view of suppressing increase and variation in probe impedance even more, preferably, the embodiment shown in FIG. 5A to 5B is used.

Second Modified Example

Figure 6:
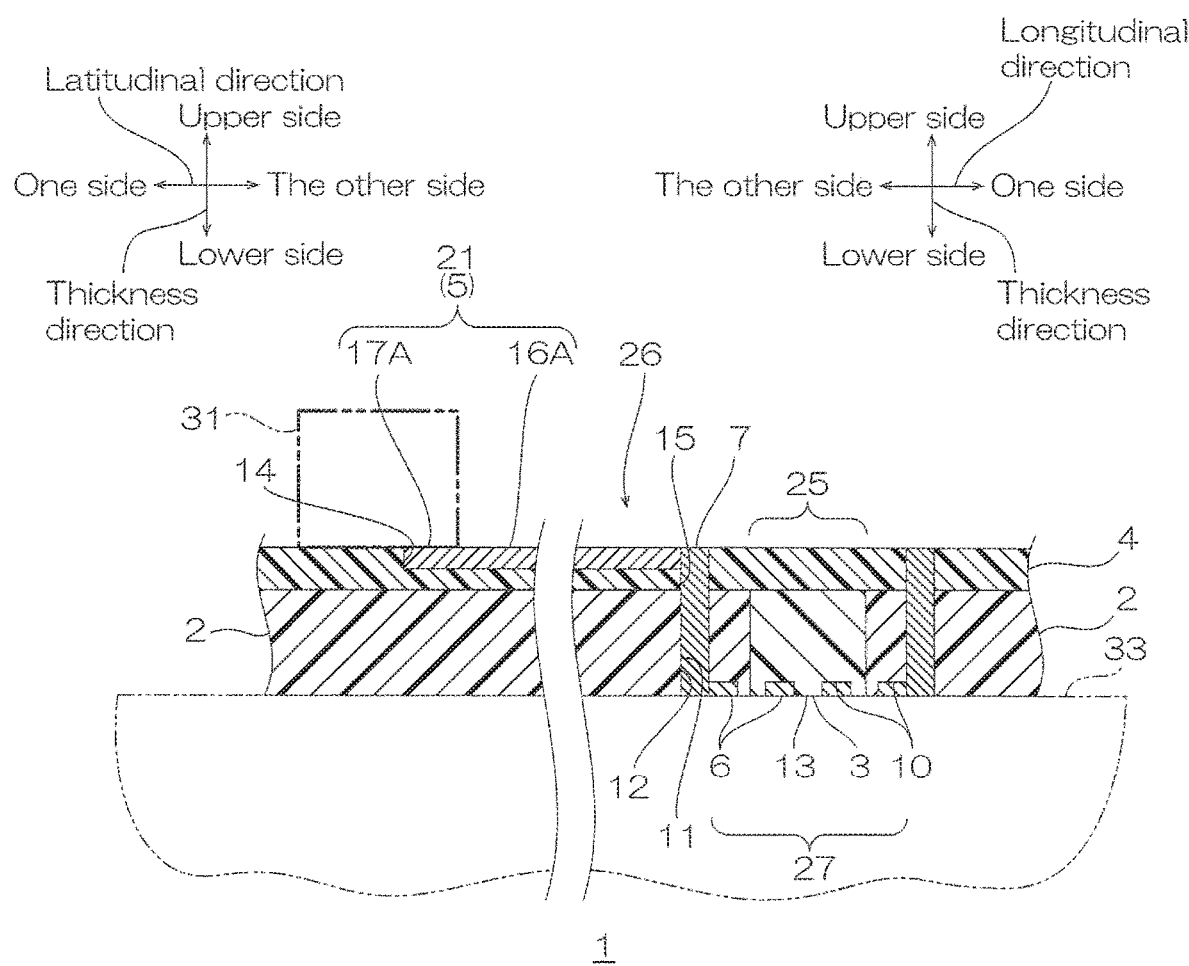
FIG. 6 shows a cross-sectional view of a modified example of the laminate for biosensor in the first embodiment (embodiment in which moisture barrier layer is smaller than probe).

As shown in FIG. 6, in the embodiment shown in FIG. 1, the contour of the moisture barrier layer 3 coincides with the contour of the probe 6 when projected in the thickness direction, but for example, the moisture barrier layer 3 may be included in the probe 6 when projected in the thickness direction. That is, the contour of the moisture barrier layer 3 may be smaller than the contour of the probe 6 in plan view, and the above-described ratio (A1/A3) is less than 1.

In view of reliably suppressing the moisture permeation at the entire probe 6 in plan view and suppressing increase and variation in impedance, preferably, the embodiment shown in FIG. 1 and FIGS. 5 A to 5B is used.

Third Modified Example

In the embodiment shown in FIG. 1, the probe 6 has a mesh shape in plan view including an exposure region 13, but for example, although not shown, the probe 6 may have a shape having no exposure region 13 (for example, a generally rectangular shape in plan view).

Preferably, the embodiment shown in FIG. 1 is used. In the embodiment shown in FIG. 1, the lower face of the moisture barrier layer 3 having pressure-sensitive adhesiveness, where the lower face is exposed at the exposure region 13 of the probe 6, makes contact with the skin 33 of a living body. Thus, the probe 6 can be brought into contact with the skin 33 of a living body uniformly and reliably, and more accurate sensing can be performed.

Fourth Modified Example

Figure 7:
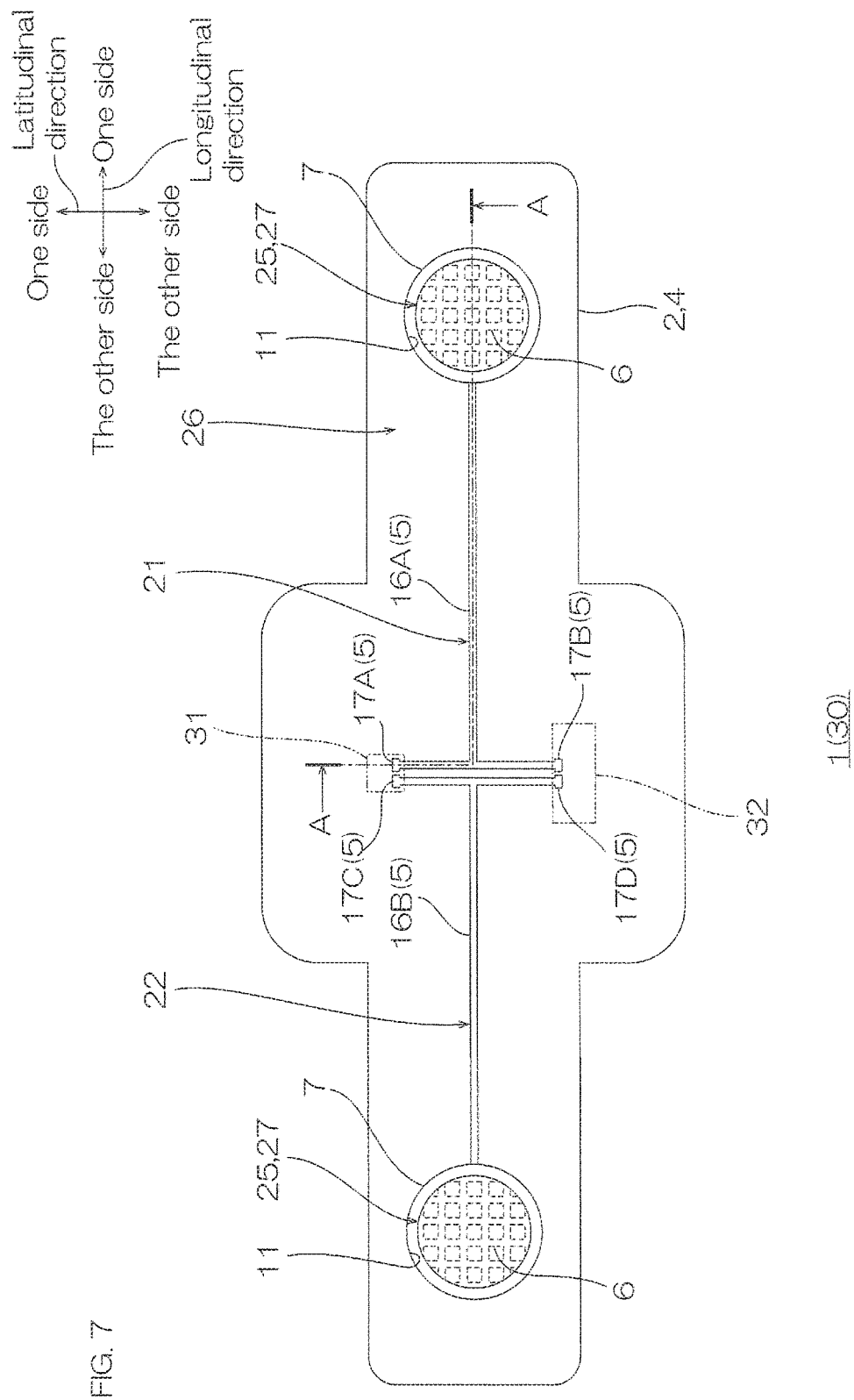
FIG. 7 shows a plan view of a modified example of the laminate for biosensor in the first embodiment (embodiment in which the probe contour is circular in plan view).

In the embodiment shown in FIG. 1, the contour of the probe 6 has a generally rectangular shape in plan view and the connecter 7 has a generally rectangular frame shape in plan view, but for example, as shown in FIG. 7, the contour of the probe 6 may have a generally circular shape in plan view, and the connecter 7 may have a generally ring shape in plan view.

Fifth Modified Example

Figure 8:
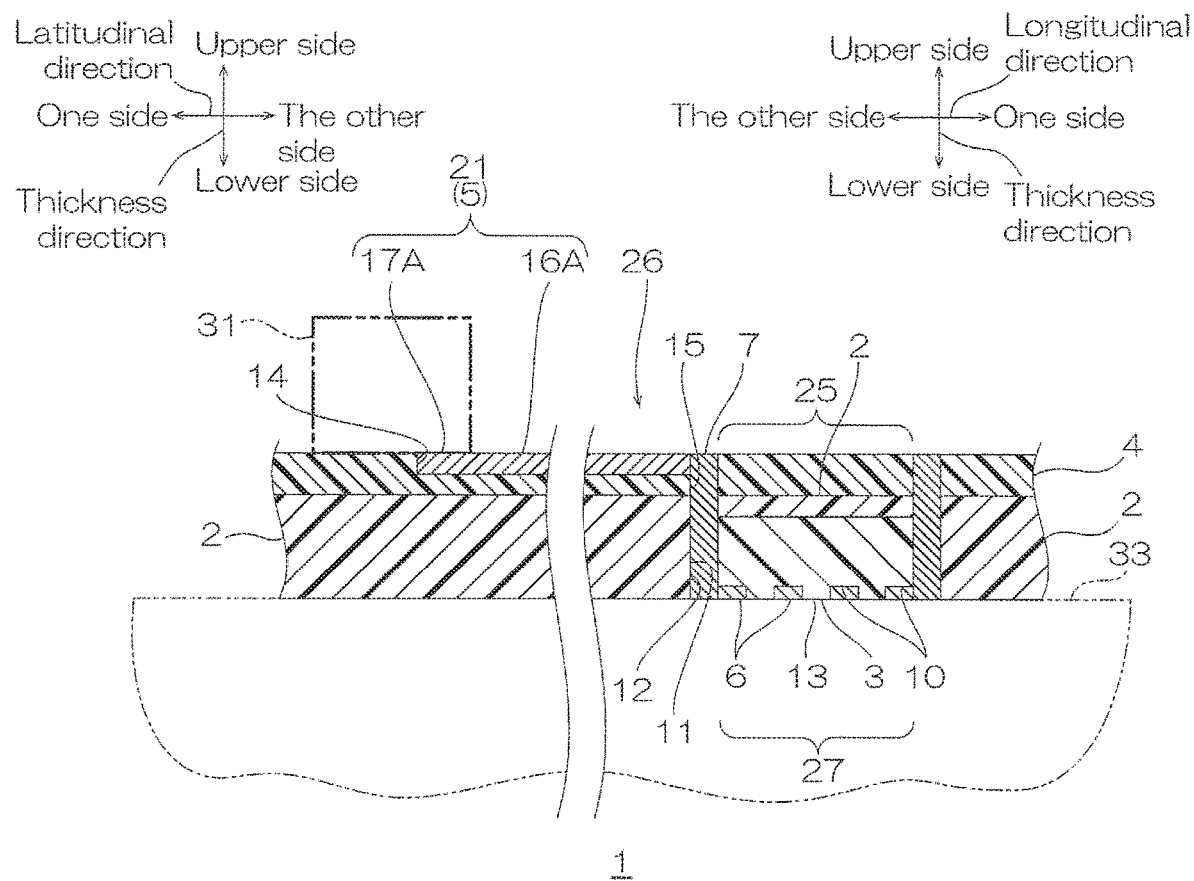
FIG. 8 shows a cross-sectional view of a modified example of the laminate for biosensor in the first embodiment (embodiment in which pressure-sensitive adhesive layer is disposed between moisture barrier layer and substrate layer).

In the embodiment shown in FIG. 1, the substrate layer 4 is disposed on the upper face of the moisture barrier layer 3, but for example, as shown in FIG. 8, the pressure-sensitive adhesive layer 2 may be interposed between the moisture barrier layer 3 and substrate layer 4. That is, in the embodiment shown in FIG. 8, the moisture barrier layer 3, the pressure-sensitive adhesive layer 2 disposed on the upper face of the moisture barrier layer 3, and the substrate layer 4 disposed on the upper face of the pressure-sensitive adhesive layer 2 are included inside the connecter 7.

Sixth Modified Example

In the embodiment shown in FIG. 1 and FIGS. 2A to 2B, the wearable electrocardiograph 30 is given as an example of the biosensor of the present invention, but for example, those devices that can perform sensing of signals from a living body to monitor health conditions of a living body are included. Examples of devices include a wearable electroencephalograph, wearable sphygmomanometer, wearable pulse meter, wearable electromyograph, and wearable thermometer. The living body includes a human body and animals other than human, but preferably, human body.

Second Embodiment

The second embodiment of the laminate for biosensor of the present invention is described with reference to FIG. 9 to FIG. 13. In the second embodiment, those members and steps that are the same as the above-described first embodiment are designated by the same reference numerals, and detailed descriptions thereof are omitted. In the second embodiment, those members and steps that are the same as the above-described first embodiment have the same configuration (shape, material, physical property, etc.) and operations and effects as those in the embodiment unless otherwise noted.

As shown in FIG. 9 to FIG. 11E, the biosensor laminate 1 as a second embodiment includes a pressure-sensitive adhesive layer (first pressure-sensitive adhesive layer) 2, substrate layer 4, wire layer 5, probe 6, connecter 7, second pressure-sensitive adhesive layer 8, and moisture barrier layer 3. To be specific, the biosensor laminate 1 includes a first pressure-sensitive adhesive layer 2, substrate layer 4 disposed on the upper face of the first pressure-sensitive adhesive layer 2, wire layer 5 embedded in the substrate layer 4, probe 6 embedded in the pressure-sensitive adhesive layer 2, connecter 7 that electrically connects the wire layer 5 and probe 6, second pressure-sensitive adhesive layer 8 disposed on the upper face of the substrate layer 4, and moisture barrier layer 3 disposed on the upper face of the second pressure-sensitive adhesive layer 8.

(First Pressure-Sensitive Adhesive Layer)

Figure 9:
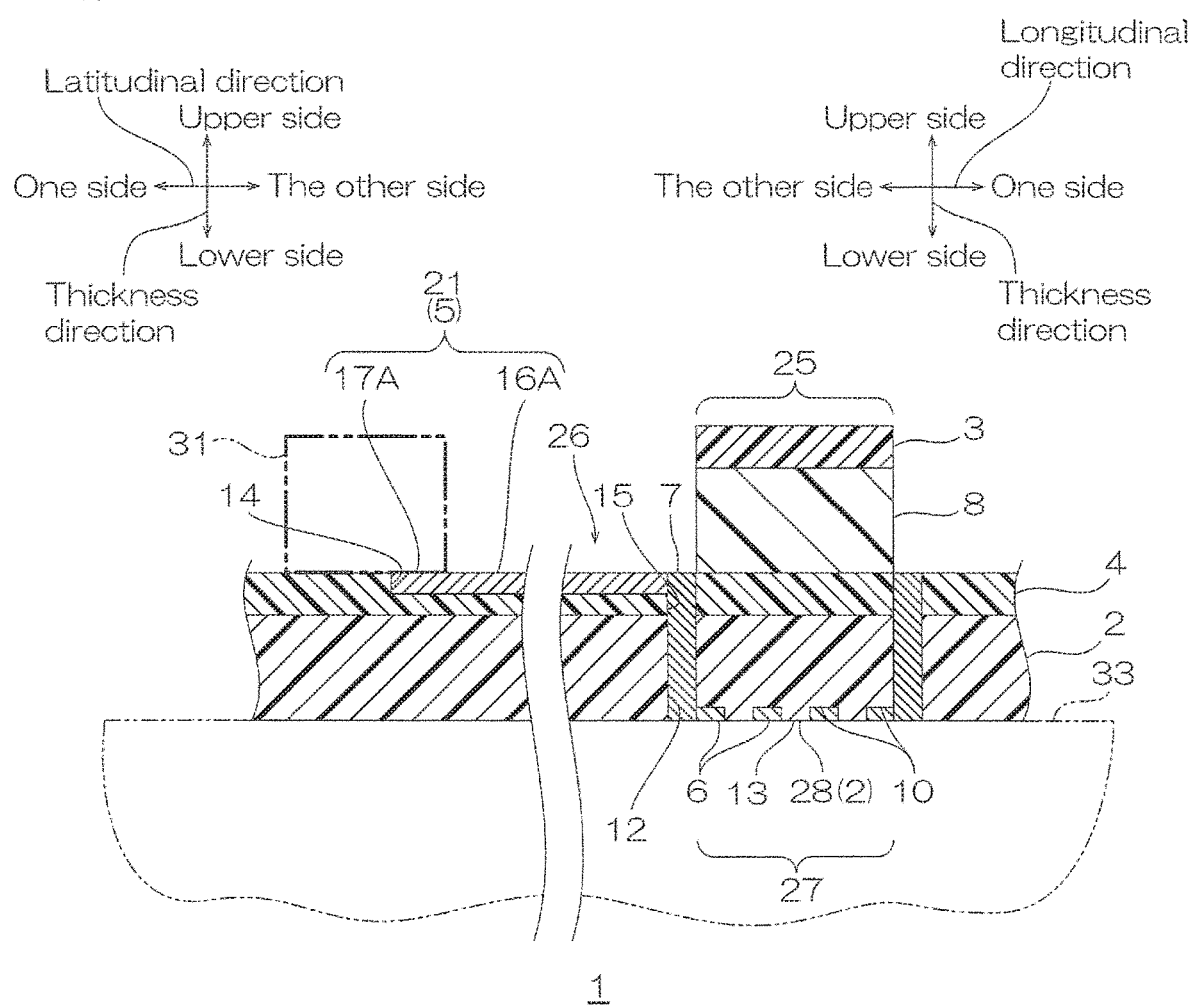
FIG. 9 shows a cross-sectional view of the laminate for biosensor of the present invention in a second embodiment.

As shown in FIG. 9, the first pressure-sensitive adhesive layer 2 forms the lower face of the biosensor laminate 1. The first pressure-sensitive adhesive layer 2 forms the contour of the biosensor laminate 1.

The first pressure-sensitive adhesive layer 2 has a frame adhesion opening 12 at both end portions in longitudinal direction thereof. The first pressure-sensitive adhesive layer 2 also has a pressure-sensitive adhesive layer (pressure-sensitive adhesive layer 28 for probe) having a generally rectangular shape in plan view inside the frame adhesion opening 12. The frame adhesion opening 12 is filled with the connecter 7. The lower face of the pressure-sensitive adhesive layer (pressure-sensitive adhesive layer 28 for probe) inside the frame adhesion opening 12 has an adhesion groove 10 corresponding to the probe 6.

(Substrate Layer)

As shown in FIG. 9, the substrate layer 4 forms the upper face of the biosensor laminate 1. The substrate layer 4 forms the contour of the biosensor laminate 1 along with the pressure-sensitive adhesive layer 2. The shape of the substrate layer 4 in plan view is the same as the shape of the pressure-sensitive adhesive layer 2 in plan view.

(Wire Layer)

Figure 10:
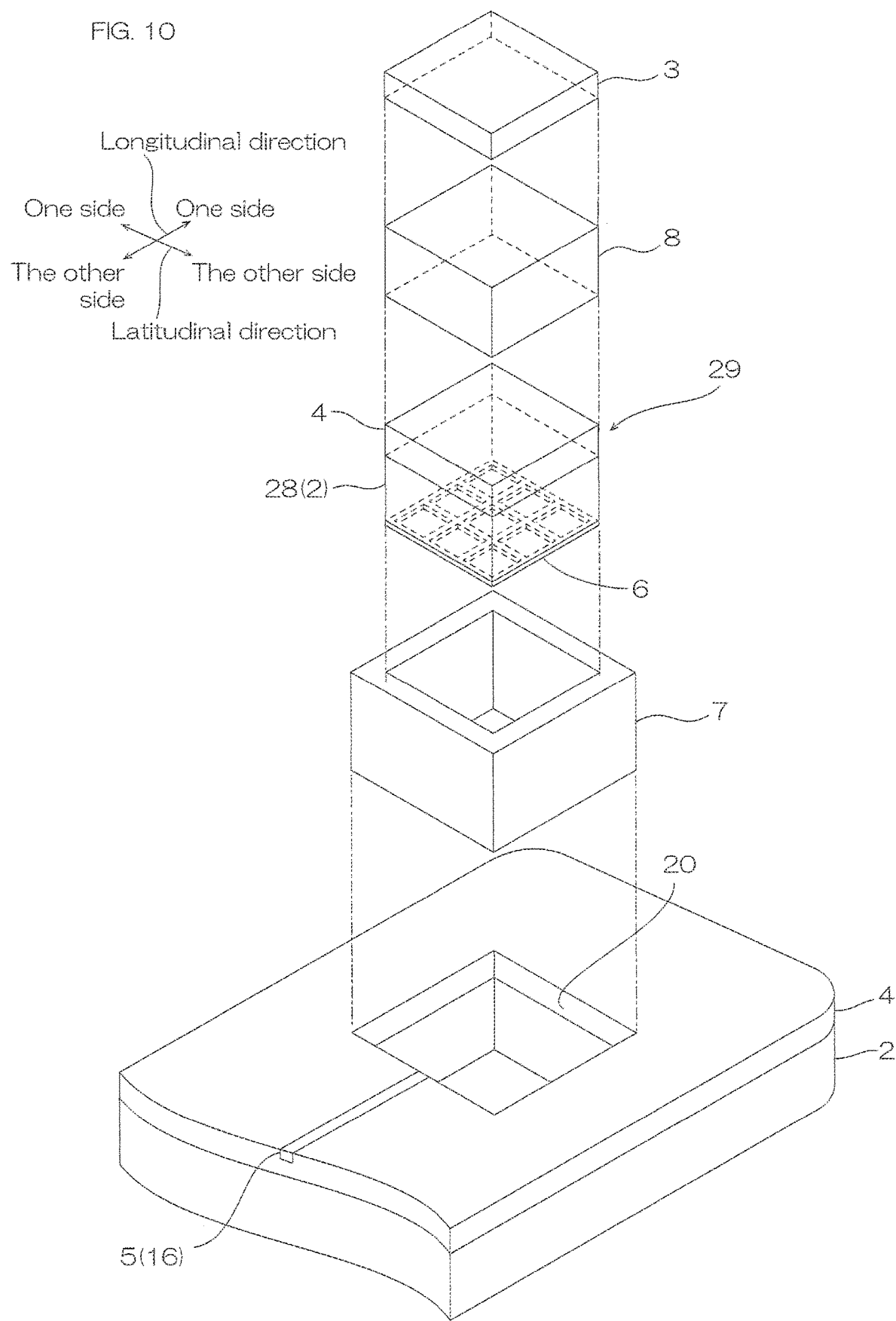
FIG. 10 shows an exploded perspective view of the probe and its surroundings of the laminate for biosensor shown in FIG. 9.

The wire layer 5 is embedded in the substrate groove 14, as shown in FIGS. 9 to 10.

(Probe)

The probe 6 is embedded in the adhesion groove 10 of the first pressure-sensitive adhesive layer 2, as shown in FIGS. 9 to 10. To be specific, the probe 6 is embedded at a lower end portion of the pressure-sensitive adhesive layer 28 for probe inside the connecter 7.

(Connecter)

The connecter 7 is provided, as shown in FIGS. 9 to 10, in correspondence with the frame substrate opening 15 and frame adhesion opening 12, and has the same shape as those.

The internal face of the connecter 7 is in contact with the probe 6, pressure-sensitive adhesive layer 2, and substrate layer 4; and the external face of the connecter 7 is in contact with the pressure-sensitive adhesive layer 2, and substrate layer 4.

(Second Pressure-Sensitive Adhesive Layer)

The second pressure-sensitive adhesive layer 8 is a layer for adhesively bonding the substrate layer 4 and the moisture barrier layer 3.

The second pressure-sensitive adhesive layer 8 is disposed at a portion of the upper face of the substrate layer 4, as shown in FIGS. 8 to 10. The second pressure-sensitive adhesive layer 8 is disposed so as to overlap with the probe 6 when projected in the thickness direction. To be specific, it is disposed so that the contour of the second pressure-sensitive adhesive layer 8 coincides with the contour of the probe 6 (also inner shape of the connecter 7) when projected in the thickness direction. That is, the contour of the second pressure-sensitive adhesive layer 8 is the same as that of the contour of the probe 6 in plan view.

For the material of the second pressure-sensitive adhesive layer 8, a material having pressure-sensitive adhesiveness is used, and for example, the material for the first pressure-sensitive adhesive layer 2 can be used, and preferably, acrylic pressure-sensitive adhesives are used.

The second pressure-sensitive adhesive layer 8 has a moisture permeability of, for example, 1 g/m²·day or more, preferably 10 g/m²·day or more, and for example, 10000 g/m²·day or less.

The second pressure-sensitive adhesive layer 8 has a thickness of, for example, 10 μm or more, preferably 20 μm or more, and for example, 300 μm or less, preferably 100 μm or less, more preferably 50 μm or less.

(Moisture Barrier Layer)

The moisture barrier layer 3 forms a portion of the upper face of the biosensor laminate 1, as shown in FIGS. 8 to 10. The moisture barrier layer 3 is disposed on the entire upper face of the second pressure-sensitive adhesive layer 8. The shape of the moisture barrier layer 3 in plan view is the same as the shape of the second pressure-sensitive adhesive layer 8 in plan view. That is, the contour of the moisture barrier layer 3 is the same as the contour of the probe 6 in plan view.

Examples of the moisture barrier layer 3 include examples described above regarding the moisture barrier layer 3 described in the first embodiment.

The upper face of the moisture barrier layer 3 preferably has no pressure-sensitive adhesiveness in view of handleability. Examples of the moisture barrier layer include, preferably, a polyolefin resin layer, acrylic resin layer, and polyvinyl resin layer; more preferably, polyolefin resin layer and acrylic resin layer; and even more preferably, polyolefin resin layer.

The moisture permeability of the moisture barrier layer 3 is the same as that of the first embodiment. Area A1 of the barrier region 25 is generally the same as area A3 of the probe region 27, as in the first embodiment.

The moisture barrier layer 3 has a thickness of, for example, 5 μm or more, preferably 10 μm or more, and for example, 3000 μm or less, preferably 2000 μm or less.

(Method for Producing Biosensor Laminate)

Next, description is given below of the method for producing a biosensor laminate 1 in an embodiment with reference to FIG. 11A to FIG. 11E.

In this method, in the same manner as in the first embodiment, first, the substrate layer 4 and wire layer 5 are prepared (ref: FIG. 4A, FIG. 11A), and then the pressure-sensitive adhesive layer 2 is disposed on the lower face of the substrate layer 4 (ref: FIG. 4B, FIG. 11B).

Then, the laminate opening 20 is formed on the pressure-sensitive adhesive layer 2 and substrate layer 4 (ref: FIG. 4C, FIG. 11C).

Thereafter, a second probe member 29 is prepared, and inserted into the laminate opening 20.

As shown in FIG. 10, the second probe member 29 includes a probe 6, a first pressure-sensitive adhesive layer 2 in which the probe 6 is embedded, and a substrate layer 4 disposed on the upper face of the first pressure-sensitive adhesive layer 2. Preparation of the second probe member 29 is conducted in the same manner as in the preparation of the first probe member 18, except that the material of the moisture barrier layer 3 is changed to the material of the first pressure-sensitive adhesive layer 2.

As shown in FIG. 11D, then, the connecter 7 is provided inside the frame substrate opening 15 and frame adhesion opening 12.

As shown in FIG. 11E, then, the second pressure-sensitive adhesive layer 8 and moisture barrier layer 3 are disposed in this order on the upper face of the substrate layer 4.

First, the second pressure-sensitive adhesive layer 8 is disposed on a release sheet, and the second pressure-sensitive adhesive layer 8 is bonded to the substrate layer 4, and thereafter, the release sheet is removed from the second pressure-sensitive adhesive layer 8. This is conducted in the same manner as in the method of disposing the pressure-sensitive adhesive layer 2 on the substrate layer 4 in the first embodiment.

Then, the moisture barrier layer 3 is bonded to the second pressure-sensitive adhesive layer 8 by, for example, lamination. To be specific, the lower face of the moisture barrier layer 3 is brought into contact with the upper face of the second pressure-sensitive adhesive layer 8.

The lower face of the second pressure-sensitive adhesive layer 8 may be bonded to the upper face of the substrate layer 4 after the upper face of the second pressure-sensitive adhesive layer 8 is bonded to the moisture barrier layer 3.

The biosensor laminate 1 is produced in this manner.

The thus produced biosensor laminate 1 includes a release sheet 19, first pressure-sensitive adhesive layer 2, substrate layer 4, wire layer 5, probe 6, connecter 7, second pressure-sensitive adhesive layer 8, and moisture barrier layer 3. The biosensor laminate 1 may be composed of the first pressure-sensitive adhesive layer 2, substrate layer 4, wire layer 5, probe 6, connecter 7, second pressure-sensitive adhesive layer 8, and moisture barrier layer 3 without including the release sheet 19, as shown in FIG. 2A and FIG. 2B.

The biosensor laminate 1 of the second embodiment achieves the same operations and effects as those of the biosensor laminate 1 in the first embodiment. Preferably, in view of suppressing increase and variation in impedance even more, and in view of even more excellent wearability, laminate for biosensor in the first embodiment is used.

In the biosensor laminate 1, the moisture barrier layer 3 is disposed at the upper side of the substrate layer 4. Therefore, the moisture barrier layer 6 can be disposed easily on the upper side of the substrate layer 4 through the second pressure-sensitive adhesive layer 8. Therefore, production suitability is excellent.

The biosensor laminate 1 in the second embodiment may be used, for example, a wearable electrocardiograph 30 as an example of the biosensor. The wearable electrocardiograph 30, in which the biosensor laminate 1 of the second embodiment is used, the method of using it and operations and effects are the same as the wearable electrocardiograph 30, in which the biosensor laminate 1 in the first embodiment is used, the method of using it and Operations and effects.

Modified Example

In the modified examples below, the members and steps corresponding to those described in the embodiment above are designated by the same reference numerals, and detailed descriptions thereof are omitted. These modified examples can be suitably combined. Furthermore, the modified examples have the same operations and effects as those in the embodiment unless otherwise noted.

First Modified Example

In the embodiment shown in FIG. 9, the contour of the moisture barrier layer 3 coincides with the contour of the probe 6 when projected in the thickness direction, but for example, as shown in FIGS. 12 A to 12B, the moisture barrier layer 3 can include the probe 6 when projected in the thickness direction. That is, the contour of the moisture barrier layer 3 can be larger than the contour of the probe 6 in plan view.

At this time, the second pressure-sensitive adhesive layer 8 also has the same shape and size as those of the moisture barrier layer 3.

Area A1 of the barrier region 25 is larger than area A3 of the probe region 27, to be specific, it is the same as in the first modified example of the first embodiment.

In view of excellent wearability, preferably, the embodiment shown in FIG. 9 is used. Meanwhile, in view of suppressing increase and variation in impedance even more, preferably, the embodiment shown in FIGS. 12 A to 12B is used.

Second Modified Example

Figure 13:
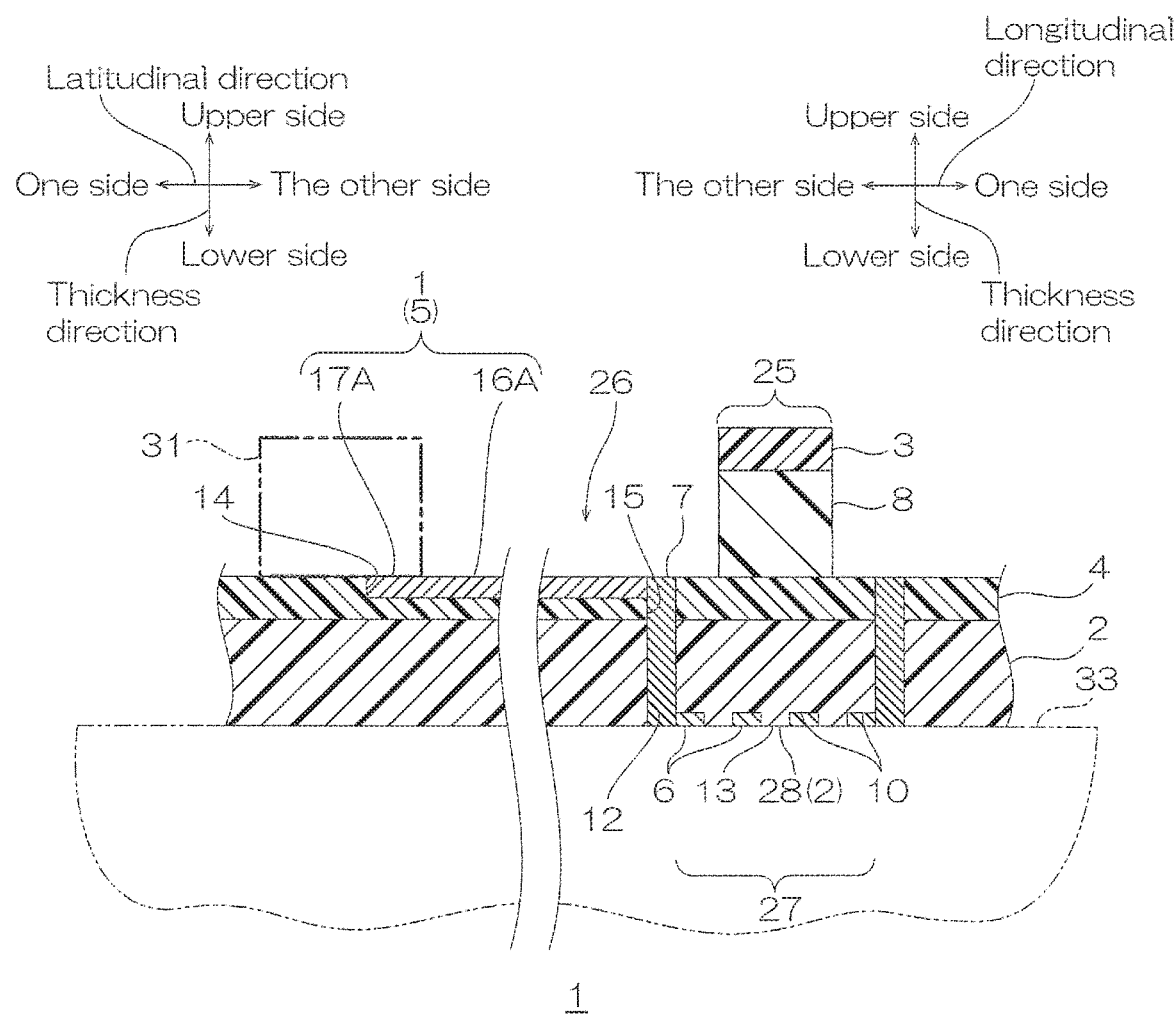
FIG. 13 shows a cross-sectional view of a modified example of the laminate for biosensor of the second embodiment (embodiment in which moisture barrier layer is smaller than probe).

In the embodiment shown in FIG. 9, as shown in FIG. 13, the contour of the moisture barrier layer 3 coincides with the contour of the probe 6 when projected in the thickness direction, but for example, the moisture barrier layer 3 can be included in the probe 6 when projected in the thickness direction. That is, the contour of the moisture barrier layer 3 can be smaller than the contour of the probe 6 in plan view.

At this time, the second pressure-sensitive adhesive layer 8 also has the same shape and size as those of the moisture barrier layer 3.

Figure 12A:
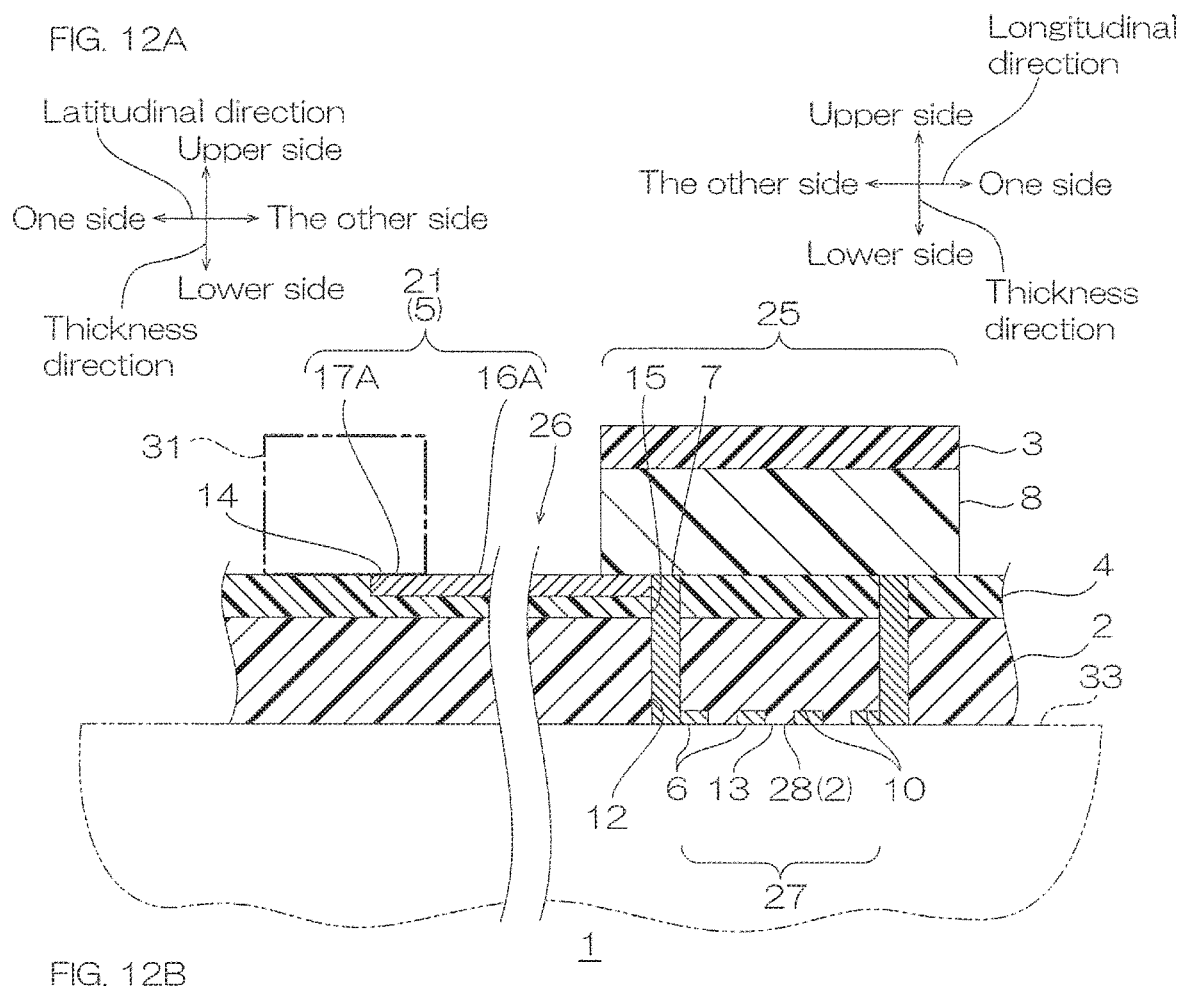
FIG. 12A to FIG. 12B show a modified example of the laminate for biosensor of the second embodiment (embodiment in which moisture barrier layer is larger than probe)
Figure 12B:
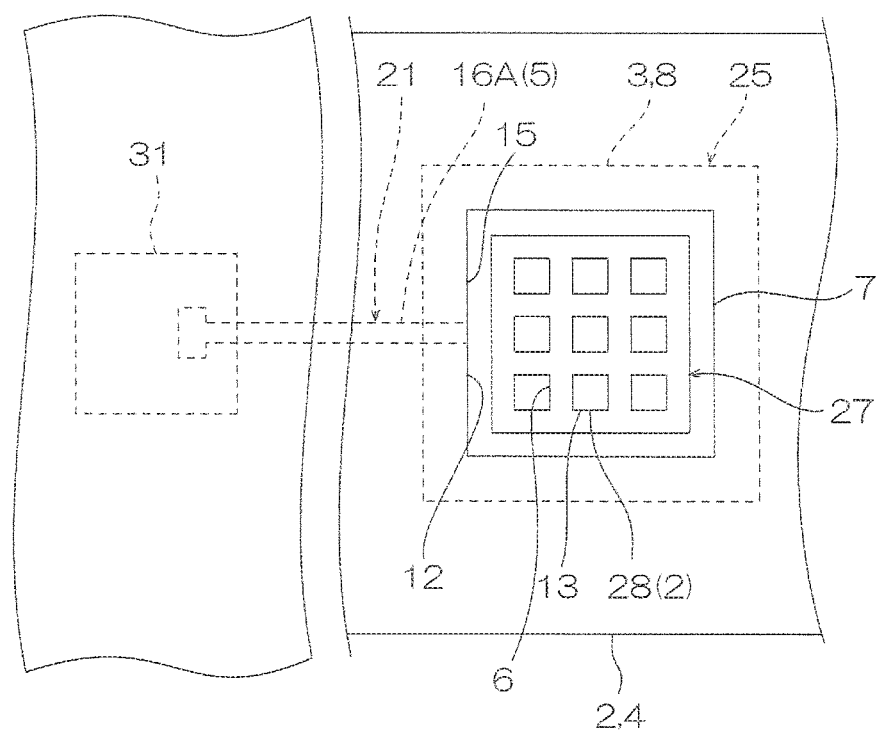

In view of reliably suppressing permeation of moisture in the entirety of the probe 6 in plan view, and increase and variation in impedance, preferably, the embodiment shown in FIG. 9 and FIGS. 12A to 12B is used.

Other Modified Examples

The third modified example, fourth modified example, and sixth modified example of the first embodiment can also be applied to a modified example of the second embodiment, and their operations and effects are the same.

Third Embodiment

A third embodiment of the laminate for biosensor of the present invention is described with reference to FIG. 14. In the second embodiment, those members and steps that are the same as those in the above-described first embodiment are designated by the same reference numerals, and detailed descriptions thereof are omitted. In the third embodiment, those members and steps that are the same as the above-described first embodiment have the same configuration (shape, material, physical property, etc.) and operations and effects as those in the first embodiment unless otherwise noted.

As shown in FIG. 14, the biosensor laminate 1 in third embodiment includes a pressure-sensitive adhesive layer (first pressure-sensitive adhesive layer) 2, substrate layer 4, wire layer 5, probe 6, connecter 7, and moisture barrier layer 3. To be specific, the biosensor laminate 1 includes a first pressure-sensitive adhesive layer 2, substrate layer 4 disposed on the upper face of the first pressure-sensitive adhesive layer 2, wire layer 5 embedded in the substrate layer 4, probe 6 embedded in the pressure-sensitive adhesive layer 2, connecter 7 that electrically connects the wire layer 5 and the probe 6, and moisture barrier layer 3 disposed on the lower face of the probe 6 and pressure-sensitive adhesive layer 2.

The moisture barrier layer 3 in the third embodiment has electrical conductivity. In this manner, water can be kept at the interface between the skin of a living body 33 and the moisture barrier layer 3, while allowing conductivity with the probe 6.

For the material of the electrically conductive moisture barrier layer 3, an electrically conductive particle-containing composition in which known electrically conductive particles are blended to a rubber composition such as the above-described polyisobutylene composition is used.

The contour of the moisture barrier layer 3 coincides with the contour of the probe 6 when projected in the thickness direction.

Preferably, the biosensor laminate 1 of the first embodiment and second embodiment is used. With the biosensor laminate 1, electrically conductive particles are not necessary for the material of the moisture barrier layer 3, and materials for the moisture barrier layer can be selected freely. As a result, a material with high moisture barrier properties can be selected. Furthermore, the lower face of the biosensor laminate 1 can be made flat entirely, and therefore it can be attached to a living body excellently.

The first to fourth modified examples and sixth modified example of the first embodiment can also be applied to the third embodiment as modified examples, and their operations and effects are the same.

EXAMPLES

Hereinafter, the present invention is described in further detail with reference to Examples and Comparative Examples. However, the present invention is not limited to those described in Examples and Comparative Examples. The specific numerical values of mixing ratio (content), physical property value, and parameter used in the description below can be replaced with the upper limit values (numerical values defined with "or less" or "below") or lower limit values (numerical values defined with "or more" or "more than") of the corresponding numerical values of mixing ratio (content), physical property value, and parameter described in "DESCRIPTION OF EMBODIMENTS" above.

Example 1

Figure 15:
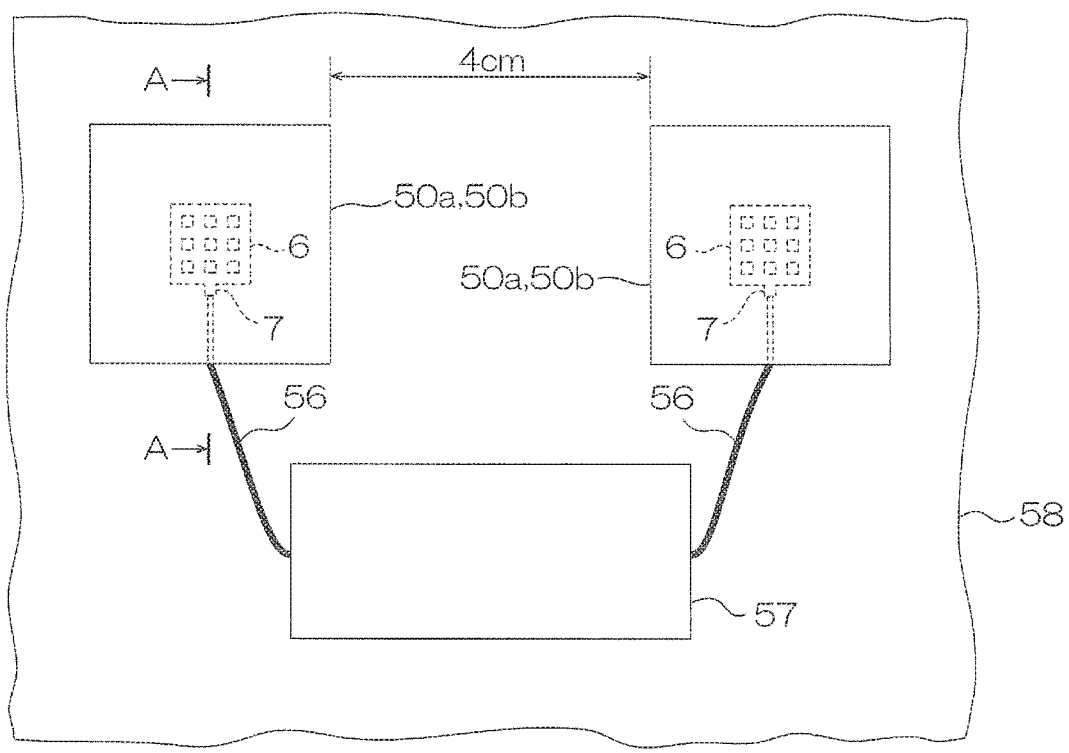
FIG. 15 shows a scheme for impedance measurement test in Examples.
Figure 16A:
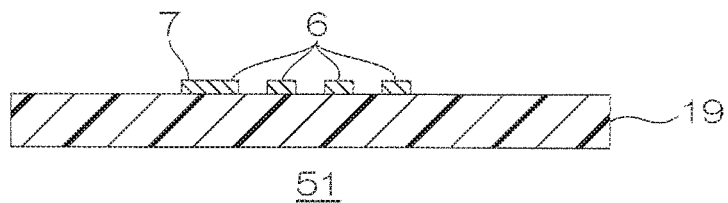
FIG. 16A to FIG. 16E are a process diagram for production of a sample for impedance measurement in Example 1 (cross sectional view taken along A-A in FIG. 15)
Figure 16B:
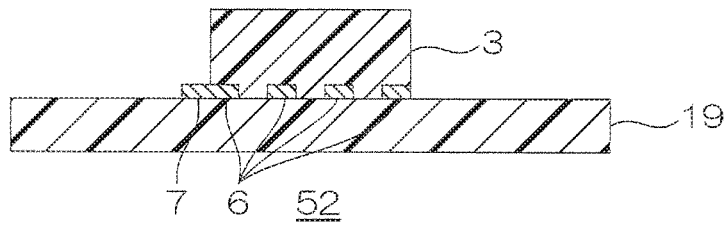
Figure 16C:
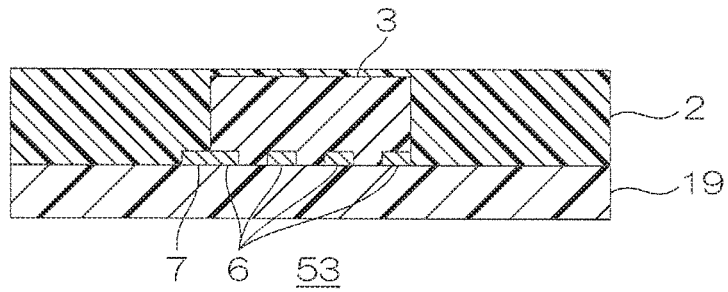
Figure 16D:
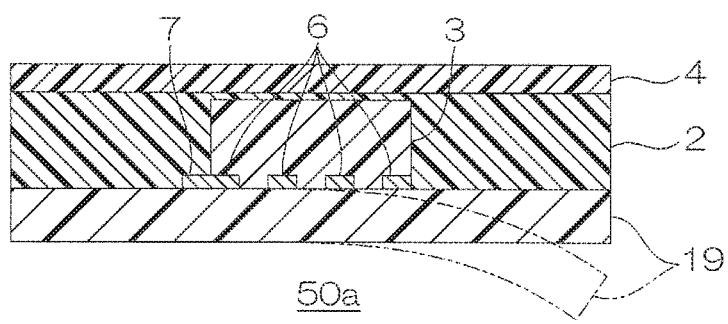
Figure 16E:
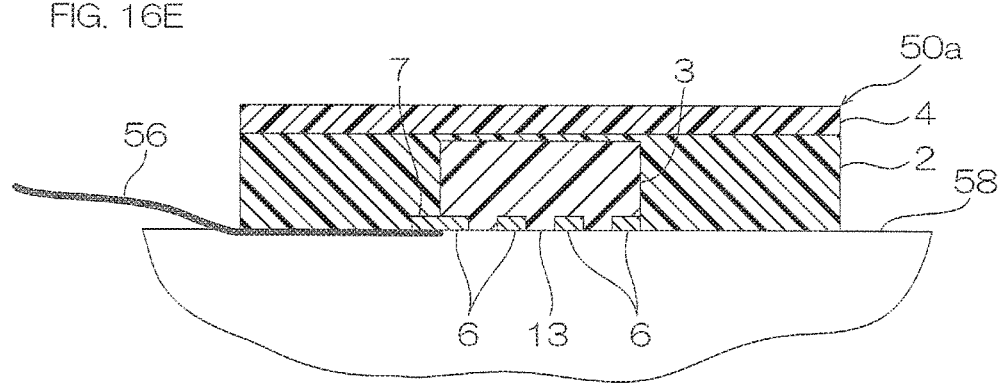

To conduct the test shown in FIG. 15, an impedance measurement sample 50a shown in FIG. 16D is prepared.

To be specific, first, a polyethylene terephthalate (PET) film (3 cm×3 cm) was prepared as the release sheet 19.

An application liquid of the electrical conductive resin composition was prepared by mixing 19 g of 1% aqueous solution of electrical conductive polymer ("Clevious PH 1000", containing PEDOT-PSS, manufactured by Heraeus), 5 g of 10% aqueous solution modified polyvinyl alcohol ("Gohsenol Z410", manufactured by The Nippon Synthetic Chemical Industry Co., Ltd.), 0.1 g of 10% aqueous solution of zirconium cross-linking agent ("Safelink SPM-1", manufactured by Mitsubishi Chemical Corporation), 1 g of glycerine (plasticizer, manufactured by Wako Pure Chemical Industries, Ltd.), and 0.04 g of silicone surfactant ("SIL-FACE SA503A", manufactured by Nissin Chemical Industry Co., Ltd.). The application liquid was applied on the upper face of the PET film so that a probe 6 having a grid shape in plan view (length 1 cm×width 1 cm, thickness 10 µm) and projected connecter 7 were formed, and then cured by heating. In this manner, a probe sheet 51 was produced (ref: FIG. 16A).

Then, 23 parts by mass of polyisobutylene (50 mass % of "OPPANOL N80", manufactured by BASF, 50 mass % of "Tetrax 5T", manufactured by JXTG energy), 23 parts by mass of liquid polybutene ("HV-300", manufactured by JXTG energy), 4 parts by mass of crosslinked sodium salt of isobutylene-maleic anhydride copolymer ("KI gel", manufactured by Kuraray Trading Co., Ltd.), 23 parts by mass of petroleum resin ("Escorez™ 1202U", manufactured by EMG Marketing G.K.), 4 parts by mass of hexamethylene diisocyanate ("BASONAT HA2000", manufactured by BASF), and 23 parts by mass of calcium carbonate heavy (manufactured by Maruo calcium Co., Ltd.) were diluted with toluene solvent, thereby preparing a polyisobutylene composition solution. The polyisobutylene composition solution was applied to a second release sheet (PET film), and dried by heating. A moisture barrier layer sheet including the pressure-sensitive adhesiveness was produced in this manner. The moisture barrier layer 3 had a generally rectangular shape in plan view (1 cm×1 cm, thickness 25 μm).

Then, the moisture barrier layer sheet was disposed on the probe sheet 51 so that the probe 6 was embedded in the moisture barrier layer 3, and the second release sheet was released from the moisture barrier layer 3. At this time, the moisture barrier layer 3 was disposed so that the contour of the probe 6 coincided with the contour of the moisture barrier layer 3. In this manner, a first laminate 52 including the moisture barrier layer 3, probe sheet 51, and release sheet 19 is produced (ref: FIG. 16B).

Then, 65 parts by mass of acrylic acid isononyl, 30 parts by mass of acrylic acid methoxy ethyl, and 5 parts by mass of acrylic acid were copolymerized to prepare acrylic polymer. Then, 100 parts by mass of the acrylic polymer, 60 parts by mass of capric triglyceride (trade name "COCONARD", manufactured by Kao Corporation), and 0.01 parts by mass of polyfunctional isocyanate (trade name "CORONATER HL", manufactured by Nippon Polyurethane Industry Co., Ltd.) were stirred and mixed, thereby preparing an acrylic pressure-sensitive adhesive composition. Then, the acrylic pressure-sensitive adhesive composition was applied on the upper face of the third release sheet (PET film), and then dried by heating. The pressure-sensitive adhesive layer sheet was produced in this manner. The pressure-sensitive adhesive layer 2 had a generally rectangular shape in plan view (3 cm×3 cm, thickness 25 μm).

Then, the pressure-sensitive adhesive layer sheet was disposed on the first laminate 52 so that the moisture barrier layer 3 is embedded in the pressure-sensitive adhesive layer 2, and the third release sheet was released from the moisture barrier layer 3. At this time, the pressure-sensitive adhesive layer 2 was disposed so that the center of the contour of the probe 6 coincide with the center of the contour of the pressure-sensitive adhesive layer 2. In this manner, the second laminate 53 including a pressure-sensitive adhesive layer 2, moisture barrier layer 3, probe 6, and release sheet 19 was produced (ref: FIG. 16 C). In the second laminate 53, the thickness of the moisture barrier layer 3 is substantially the same as that of the moisture barrier layer 3 before lamination, and the pressure-sensitive adhesive layer 2 disposed on the upper face of the moisture barrier layer 3 had a thickness of about less than about 1 μm.

Then, the polyurethane-containing solution (trade name "PANDEX T-8180N", manufactured by DIC Covestro Polymer Ltd.) was stirred and mixed with capric triglyceride ("trade name COCONARD", manufactured by Kao Corporation) so that the mass ratio (solid content) of "polyurethane:capric triglyceride" was 100:10, thereby preparing a substrate composition solution. The substrate composition solution was applied on the upper face of the fourth release sheet, and then dried by heating. The substrate layer sheet was produced in this manner. The substrate layer 4 had a size of 3 cm×3 cm and a thickness of 8 μm.

Then, the substrate layer sheet was disposed on the second laminate so that the substrate layer 4 was allowed to contact the pressure-sensitive adhesive layer 2 pressure-sensitively, and the fourth release sheet was released from the pressure-sensitive adhesive layer 2.

In this manner, the measurement sample 50a of Example 1 including the pressure-sensitive adhesive layer 2, moisture barrier layer 3, probe 6, and release sheet 19 was produced (ref: FIG. 16 D).

Example 2

Figure 17A:
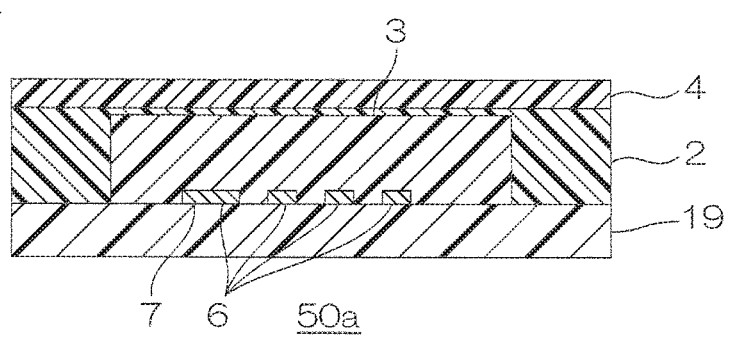
FIG. 17A to FIG. 17B show a cross sectional view of an impedance measurement sample in Examples.
Figure 17B:
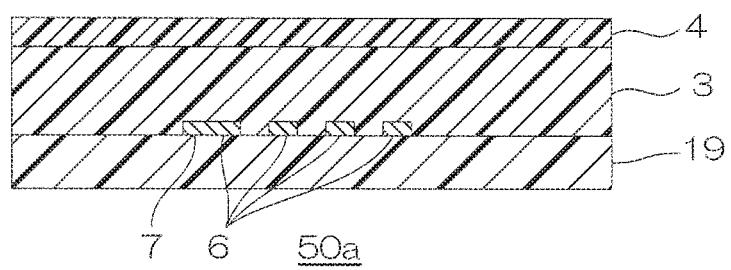

The measurement sample 50a was produced in the same manner as in Example 1, except that the moisture barrier layer 3 had a generally rectangular shape in plan view with 2 cm×2 cm (ref: FIG. 17 A).

Example 3

The measurement sample 50a was produced in the same manner as in Example 1, except that the moisture barrier layer 3 had a generally rectangular shape in plan view of 3 cm×3 cm, and the pressure-sensitive adhesive layer 2 was not used (ref: FIG. 17 B).

Example 4

The measurement sample 50a was produced in the same manner as in Example 3, except that a natural rubber-SBR mixed resin layer (product "drape tape", manufactured by Nitto Denko Corporation) was used as the moisture barrier layer 3, and the thickness was set to 25 μm (ref: FIG. 17 B).

Example 5

The measurement sample 50a was produced in the same manner as in Example 3, except that a SBR resin layer (product "SLY-25", manufactured by Nitto Denko Corporation) was used as the moisture barrier layer 3, and the thickness was set to 25 μm (ref: FIG. 17 B).

Example 6

Figure 18A:
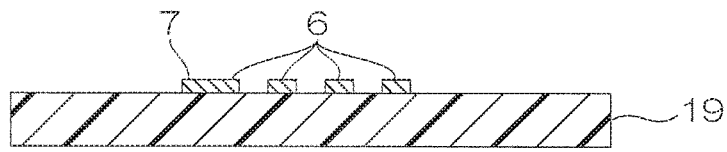
FIG. 18A to FIG. 18E are a process diagram for production of an impedance measurement sample in Example 4 (cross sectional view taken along A-A in FIG. 15)
Figure 18B:
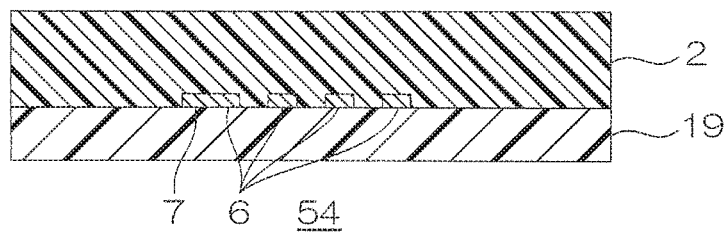
Figure 18C:
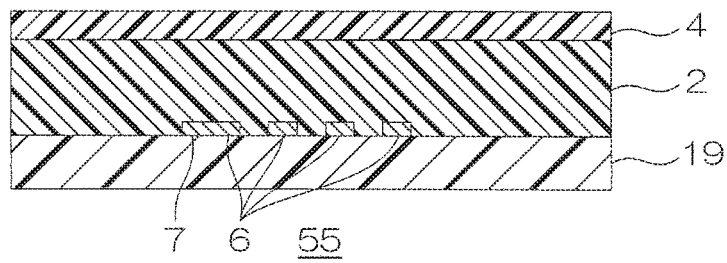
Figure 18D:
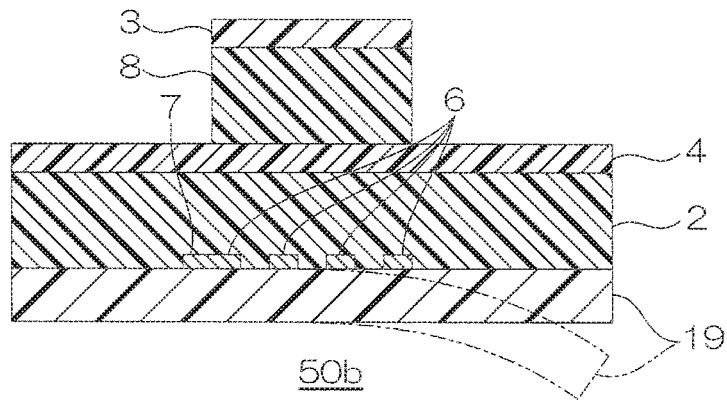
Figure 18E:
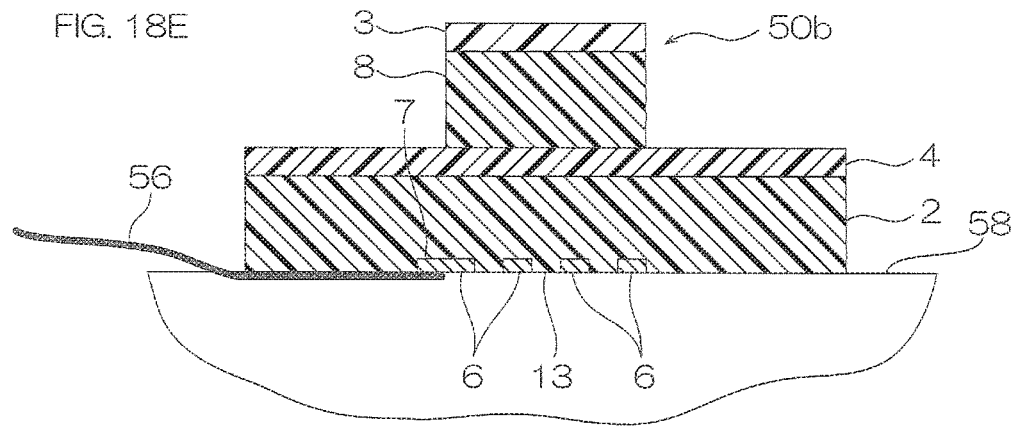

The impedance measurement sample 50b shown in FIG. 18D was produced.

To be specific, first, a probe sheet 51 of Example 1 was prepared (ref: FIG. 18 A).

The pressure-sensitive adhesive layer sheet of Example 1 (first pressure-sensitive adhesive layer: 3 cm×3 cm, thickness 25 μm) was prepared. The pressure-sensitive adhesive layer sheet was disposed on the probe sheet 51 so that the probe 6 was embedded in the pressure-sensitive adhesive layer 2, and the second release sheet was released from the probe 6. In this manner, a second-first laminate 54 including the release sheet 19, probe 6, and first pressure-sensitive adhesive layer 2 was produced (ref: FIG. 18 B).

The substrate layer sheet of Example 1 (substrate layer 4 cm×3 cm, thickness 8 μm) was prepared. The substrate layer sheet was disposed on the second-first laminate 54 so that the substrate layer 4 was in contact with the pressure-sensitive adhesive layer 2 pressure-sensitively, and the fourth release sheet was released from the pressure-sensitive adhesive layer 2. In this manner, the second-second laminate 55 including the substrate layer 4, first pressure-sensitive adhesive layer 2, probe 6, and release sheet 19 was produced (ref: FIG. 18 C).

The pressure-sensitive adhesive layer sheet of Example 1 (second pressure-sensitive adhesive layer 8: thickness 25 µm) was prepared, except that the size was changed to 1 cm×1 cm. The pressure-sensitive adhesive layer sheet was disposed on the second-second laminate 55 so that the probe 6 and the pressure-sensitive adhesive layer coincide with each other in plan view, and the pressure-sensitive adhesive layer 2 is in contact with the substrate layer 4 pressure-sensitively; and the second release sheet was released from the pressure-sensitive adhesive layer 2. Then, a moisture barrier layer 3 (polyolefin resin layer, 1 cm×1 cm, thickness 1200 µm, "No. 576", manufactured by Nitto) was disposed on the entire face of the second pressure-sensitive adhesive layer 8.

In this manner, the measurement sample 50b of Example 6 including the moisture barrier layer 3, second pressure-sensitive adhesive layer 8, substrate layer 4, first pressure-sensitive adhesive layer 2, probe 6, and release sheet 19 was produced (ref: FIG. 18 D).

Example 7

Figure 19:
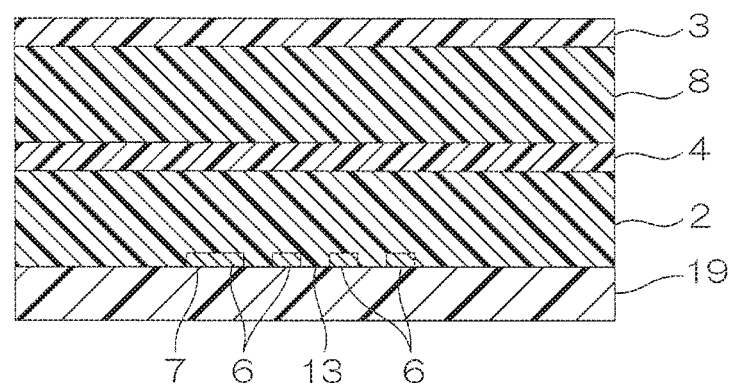
FIG. 19 shows a cross-sectional view of the impedance measurement sample in Examples 5 to 8.

The measurement sample 50b was produced in the same manner as in Example 6, except that the size of the moisture barrier layer 3 and second pressure-sensitive adhesive layer 8 were changed to 3 cm×3 cm (ref: FIG. 19).

Example 8

The measurement sample 50b was produced in the same manner as in Example 7 (ref: FIG. 19), except that in the moisture barrier layer 3, the polyolefin resin layer was changed to an acrylic resin layer (acrylic foam, 3 cm×3 cm, thickness 100 µm, "ISR-ACF-510AD", manufactured by Iwatani Corporation).

Example 9

The measurement sample 50b was produced in the same manner as in Example 7 (ref: FIG. 19), except that in the moisture barrier layer 3, the polyolefin resin layer was changed to a poly propylene resin layer (poly propylene foam, 3 cm×3 cm, thickness 1500 µm, "SCF-400", manufactured by Nitto).

Example 10

The measurement sample 50b was produced in the same manner as in Example 7 (ref: FIG. 19), except that in the moisture barrier layer 3, the polyolefin resin layer was changed to a poly vinyl alcohol resin layer (3 cm×3 cm, thickness 8 µm).

The poly vinyl alcohol resin layer was produced by drying the 10% aqueous solution of poly vinyl alcohol ("Gohsenol Z410") manufactured by Nippon Synthetic Chemical Industry Co., Ltd.

Example 11

The measurement sample 50b was produced in the same manner as in Example 6 (ref: FIG. 18 D), except that in the moisture barrier layer 3, the polyolefin resin layer was changed to the moisture barrier layer (polyisobutylene resin layer, 1 cm×1 cm, thickness 25 µm) produced in Example 1.

Comparative Example 1

A measurement sample (a laminate of substrate layer 4, first pressure-sensitive adhesive layer 2, probe 6, and release sheet 19) was produced in the same manner as in Example 6, except that the measurement sample had no second pressure-sensitive adhesive layer 8 and no moisture barrier layer 3 disposed therein.

<Measurement of Moisture Permeability>

Figure 20:
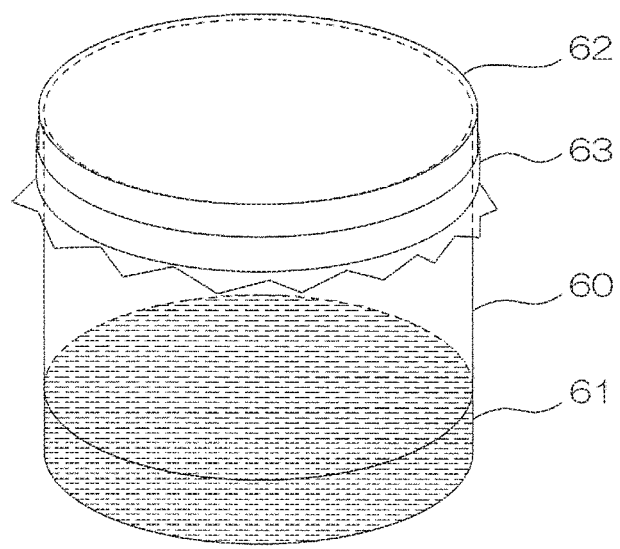
FIG. 20 shows a scheme for measuring moisture permeability.

The moisture permeability of the moisture barrier layer, pressure-sensitive adhesive layer, and substrate layer was measured based on the following procedure (ref: FIG. 20).

(1) a weighing bottle 60 with a diameter of 38 mm (opening area S: $1.13354 \times 10^{-3}$ m$^2$) and a height of 40 mm was prepared, and purified water 61 in an amount of 10 mL was put in the weighing bottle 60.

(2) The measurement sample 62 (moisture barrier layer 3, etc.) was disposed on the entire face of the opening of the measurement sample 62 so that no tension is generated in the weighing bottle 60. Then, an end portion of the measurement sample 62 was fixed to the side face of the weighing bottle 60 using an adhesive tape 63, thereby sealing the weighing bottle 60.

(3) The total mass $M_1$ of the measurement sample 62, water 61, and weighing bottle 60 immediately after the sealing was measured.

(4) The sealed weighing bottle 60 was allowed to stand under conditions of 40° C. and 30% RH for 24 hours.

(5) the total mass $M_2$ of the measurement sample 62, water 61, and weighing bottle 60 after they were allowed to stand for 24 hours was measured.

(6) the moisture permeability P was calculated using formula $[P=(M_1-M_2)/S]$.

The substrate layer (thickness 8 µm) used in Examples and Comparative Examples had a moisture permeability of 2540 g/m$^2$·day, and the pressure-sensitive adhesive layer (thickness 25 µm) had a moisture permeability of 1522 g/m$^2$·day. The moisture permeability of the moisture barrier layer is shown in Table 1.

<Impedance Measurement>

A pair of measurement samples (50a, 50b) was prepared for Examples and Comparative Examples. The release sheet 19 was released from the sample, and then each of the connecters 7 of the pair of the measurement samples was electrically connected to an impedance analyzer 57 through a lead 56, and the measurement sample was attached to a pig skin 58 (Yucatan Micropig Skinset). Upon attaching, physiological saline was dropped between the pig skin 58 and measurement sample (50a, 50b) to allow the probe 6 in initial state to be wet. The test scheme is shown in FIG. 15.

The impedance (frequency 4 Hz) between the measurement samples was measured after 0 hours, 1 hour, 2 hours, 3 hours, 4 hours, 20 hours, and 24 hours. For the impedance analyzer 57, "IM3540" (trade name) manufactured by HIOKI was used.

Table 1 shows the results thereof, the maximum impedance, and variation (difference of the maximum value and the minimum value of the measured impedance).

<Wearability Test>

The release sheet was removed from the sample of Examples and Comparative Examples, and attached to a human skin. The wearability was evaluated as follows.

Excellent: No feeling of wearing the sample even if it is worn.

Good: Feeling of wearing the sample present, but no uncomfortableness felt.

Fair: Slight feeling of uncomfortableness at the portion where it was attached, but could worn for a long period of time.

Bad: Tight feeling of skin at the portion where it was attached, and strong feeling of uncomfortableness.

<Peeling Force Measurement>

(1) Peeling Force Relative to Bakelite

The moisture barrier layer sheet (length 50 mm×width 10 mm×thickness 50 μm) of Examples and the first pressure-sensitive adhesive layer (length 50 mm×width 10 mm×thickness 50 μm) of Comparative Examples were prepared, and laminated on the entire face of a PET film (length 50 mm×width 10 mm×thickness 50 μm) to prepare samples.

The sample was allowed to contact a bakelite plate, and then a 500 g weight was allowed to go back and forth on the sample surface to be attached. After 30 minutes after the attachment, the sample was peeled under the conditions of 180° peel and a tensile speed of 300 mm/min with a peel testing machine to measure peeling force (tensile tester, "AG-1S"). The measurement was conducted three times, and the average value is shown in Table 1.

(2) Peeling Force Relative to Human Skin

The peeling force was measured in the same manner as described above, except that human skin was used instead of the bakelite plate. The results are shown in Table 1.

<Keeping Force>

The moisture barrier layer sheet of Examples (length 50 mm×width 10 mm×thickness 50 μm) and the first pressure-sensitive adhesive layer (length 50 mm×width 10 mm×thickness 50 μm) of Comparative Examples were prepared, and laminated on the entire face of a PET film (length 50 mm×width 10 mm×thickness 50 μm) to prepare a sample.

The sample was brought into contact with the Bakelite plate, and a 500 g weight was allowed to go back and forth to be attached. After 30 minutes after the attachment, a 300 g weight was put on the sample, and then the sample and Bakelite plate were put on the wall so that its longitudinal direction coincides with the vertical direction. At this time, the time when the sample fell off from the bakelite plate was measured. The results are shown in Table 1.

<Firm Attachment to Skin>

When the peeling force relative to human skin was more than 0.5 N/10 mm, and the keeping force was more than 50 minutes, it was evaluated as "Excellent." When the peeling force relative to human skin was more than 0. N/10 mm, and keeping force was 50 minutes or less, it was evaluated as "Good." When the peeling force relative to human skin was 0.5 N/10 mm or less, and keeping force was 50 minutes or less, it was evaluated as "Fair." The results are shown in Table 1.

TABLE 1

|  |  | Example 1 | Example 2 | Example 3 | Example 4 | Example 5 | Example 6 | Example 7 |
|---|---|---|---|---|---|---|---|---|
|  |  | First embodiment | | | | | Second embodiment | |
| Moisture barrier layer | Material | Poly isobutylene resin layer | Poly isobutylene resin layer | Poly isobutylene resin layer | Natural rubber-SBR resin layer | SBR resin layer | Polyolefin resin layer | Polyolefin resin layer |
|  | Area (cm$^2$) | 1 | 4 | 9 | 9 | 9 | 1 | 9 |
|  | Thickness (μm) | 25 | 25 | 25 | 50 | 50 | 1200 | 1200 |
|  | Moisture permeability (g/m$^2$ · day) | 50 | 50 | 50 | 314 | 62 | 33 | 33 |
| Impedance | Maximum value (kΩ) | 585 | 405 | 189 | 800 | 500 | 595 | 174 |
|  | Variation σ(kΩ) | 194 | 121 | 99 | 300 | 100 | 175 | 30 |
| Wearability |  | Excellent | Good | Good | Good | Good | Good | Fair |
| Peeling force (N/10 mm) | Relative to bakelite | 8.4 | 8.4 | 8.4 | 3 | 10.8 | 0.8 | 0.8 |
|  | Relative to human skin | 1.1 | 1.1 | 1.1 | 0.9 | 1.7 | 0.1 | 0.1 |
| Keeping force (min) |  | 4 | 4 | 4 | 47 | 135 | 50 | 50 |
| Stable attachment to skin |  | Good | Good | Good | Good | Excellent | Fair | Fair |

|  |  | Example 8 | Example 9 | Example 10 | Example 11 | Comp. Ex. 1 |
|---|---|---|---|---|---|---|
|  |  | Second embodiment | | | | |
| Moisture barrier layer | Material | Acrylic resin layer | Poly propylene resin layer | Poly vinyl alcohol resin layer | Poly isobutylene resin layer |  |
|  | Area (cm$^2$) | 9 | 9 | 9 | 1 |  |
|  | Thickness (μm) | 100 | 1500 | 8 | 25 |  |
|  | Moisture permeability (g/m$^2$ · day) | 208 | 559 | 768 | 50 |  |
| Impedance | Maximum value (kΩ) | 700 | 709 | 1200 | 700 | 3690 |
|  | Variation σ(kΩ) | 190 | 227 | 351 | 210 | 1400 |

TABLE 1-continued

| | | | | | | |
|---|---|---|---|---|---|---|
| Wearability | | Fair | Fair | Good | Good | Excellent |
| Peeling force (N/10 mm) | Relative to bakelite | 0.8 | 0.8 | 0.8 | 0.8 | 0.8 |
| | Relative to human skin | 0.1 | 0.1 | 0.1 | 0.1 | 0.1 |
| Keeping force (min) | | 50 | 50 | 50 | 50 | 50 |
| Stable attachment to skin | | Fair | Fair | Fair | Fair | Fair |

While the illustrative embodiments of the present invention are provided in the above description, such is for illustrative purpose only and it is not to be construed as limiting in any manner Modification and variation of the present invention that will be obvious to those skilled in the art is to be covered by the following claims.

INDUSTRIAL APPLICABILITY

The laminate for biosensor and biosensor of the present invention can be applied for various industrial products including medical and hygienic material, and for example, can be suitably used for a wearable electrocardiograph, wearable electroencephalograph, wearable sphygmomanometer, wearable pulse meter, wearable electromyograph, and wearable thermometer.

DESCRIPTION OF REFERENCE NUMERALS 1 laminate for biosensor
2 pressure-sensitive adhesive layer
3 moisture barrier layer
4 substrate layer
6 probe
13 exposure region
30 wearable electrocardiograph
31 electronic component

The invention claimed is:

1. A laminate for biosensor comprising:
a pressure-sensitive adhesive layer for attaching to a living body; and
a substrate layer disposed on an upper face of the pressure-sensitive adhesive layer, wherein
the laminate for biosensor includes
a probe disposed at a lower face of the laminate for biosensor, and
a moisture barrier layer disposed so as to overlap with the probe when projected in a thickness direction,
the probe is configured to contact a surface of the living body when the pressure-sensitive adhesive layer is attached to the surface of the living body,
the probe is embedded in the moisture barrier layer, and
the moisture barrier layer is disposed inside the pressure-sensitive adhesive layer.

2. The laminate for biosensor according to claim 1, wherein
the moisture barrier layer has a moisture permeability of 600 g/m$^2$·day or less.

3. The laminate for biosensor according to claim 1, wherein
the moisture barrier layer is disposed over a lower face of the probe.

4. The laminate for biosensor according to claim 1, wherein
the moisture barrier layer has pressure-sensitive adhesiveness.

5. The laminate for biosensor according to claim 1, wherein
the moisture barrier layer is at least one resin layer selected from the group consisting of a rubber resin layer, polystyrene resin layer, polyolefin resin layer, acrylic resin layer, and poly vinyl alcohol resin layer.

6. The laminate for biosensor according to claim 1, wherein
the probe has an exposure region that allows the pressure-sensitive adhesive layer or the moisture barrier layer to be exposed.

7. A biosensor comprising:
the laminate for biosensor according to claim 1; and
an electronic component electrically connected to the probe, and mounted on the substrate layer.

* * * * *